US012678413B2

(12) United States Patent
Park et al.

(10) Patent No.: US 12,678,413 B2
(45) Date of Patent: Jul. 14, 2026

(54) COMPOSITIONS CONTAINING PTEROSIN COMPOUND AND DERIVATIVES THEREOF ACTIVE INGREDIENTS FOR PREVENTION OR TREATMENT OF DEGENERATIVE BRAIN DISEASES

(71) Applicant: Korpharm Co., Ltd., Gyeonggi-do (KR)

(72) Inventors: Gil Hong Park, Gyeonggi-do (KR); Ali Md Yousof, Seoul (KR); Susoma Jannat, Seoul (KR); Min Ji Choi, Gyeonggi-do (KR); Seong Su Hong, Gyeonggi-do (KR); Chun Whan Choi, Gyeonggi-do (KR); Yun Hyeok Choi, Gyeonggi-do (KR); Myung Hwan Kim, Seoul (KR); Hong Kyu Kim, Seoul (KR)

(73) Assignee: Korpharm Co., Ltd., Gyeonggi-do (KR)

( * ) Notice: Subject to any disclaimer, the term of this patent is extended or adjusted under 35 U.S.C. 154(b) by 1199 days.

(21) Appl. No.: 16/622,799

(22) PCT Filed: Oct. 20, 2017

(86) PCT No.: PCT/KR2017/011666

§ 371 (c)(1),
(2) Date: Apr. 8, 2021

(87) PCT Pub. No.: WO2018/230776

PCT Pub. Date: Dec. 20, 2018

(65) Prior Publication Data

US 2022/0257532 A1 Aug. 18, 2022

(30) Foreign Application Priority Data

Jun. 16, 2017 (KR) ........................ 10-2017-0076701
Jun. 21, 2017 (KR) ........................ 10-2017-0078655

(51) Int. Cl.

| | |
|---|---|
| ***A61K 31/122*** | (2006.01) |
| ***A23L 33/10*** | (2016.01) |
| ***A61K 31/704*** | (2006.01) |
| ***A61K 36/11*** | (2006.01) |
| ***C07C 49/683*** | (2006.01) |

(52) U.S. Cl.

CPC ............ *A61K 31/122* (2013.01); *A23L 33/10* (2016.08); *A61K 31/704* (2013.01); *A61K 36/11* (2013.01); *C07C 49/683* (2013.01)

(58) Field of Classification Search

None
See application file for complete search history.

(56) References Cited

U.S. PATENT DOCUMENTS 4,754,061 A 6/1988 Cragoe, Jr. et al.

FOREIGN PATENT DOCUMENTS

| | | | | |
|---|---|---|---|---|
| CN | 101822360 | | * | 1/2013 |
| EP | 0680762 | A1 | * | 8/1995 |
| EP | 1795524 | A1 | | 6/2007 |
| EP | 2759536 | A1 | | 7/2014 |
| ES | 2088770 | | * | 9/1996 |
| WO | 9500468 | A1 | | 1/1995 |
| WO | 2010085811 | A2 | | 7/2010 |

OTHER PUBLICATIONS

Choi et al., Phytochemistry Letters, 27, 2018, 63-68.*

Potter, DM et al., "Carcinogenic Effects of Ptaquiloside in Bracken Fern and Related Compounds", British Journal of Cancer, 2000, vol. 83, No. 7, pp. 914-920.

Yoshihira, K. et al., "Chemical and Toxicological Studies on Bracken Fern, *Pteridium aquilinum* Var. *Latiusculum*. I. Introduction, Extraction and Fractionation of Constituents, and Toxicological Studies Including Carcinogenicity Tests", Chemical & Pharmaceutical Bulletin, 1978, vol. 26, No. 8, pp. 2346-2364.

Choi, Y.H. et al., "Isolation and Characterization of Seco-illudoid and Pterosin Sesquiterpenoids from Bracken Fern", Proceedings of the Spring International Convention of the Pharmaceutical Society of Korea, Apr. 20, 2017, pp. 1-857.

Chen, C.Y. et al., "Chemical Constituents Analysis and Antidiabetic Activity Validation of Four Fern Species from Taiwan", International Journal of Molecular Sciences, 2015, vol. 16, pp. 2497-2516.

Hayashi, Y. et al., "Studies on the Sesquiterpenoids of Hypolepis Punctata Mett.-I", Tetrahedron, 1977, vol. 33, No. 19, pp. 2509-2511.

International Search Report issued by ISA/KR in connection with PCT/KR2017/011666 on Apr. 12, 2018.

Written Opinion issued by ISA/KR in connection with PCT/KR2017/011666 on Apr. 12, 2018.

(Continued)

*Primary Examiner* — Michael V Meller
(74) *Attorney, Agent, or Firm* — Levenfeld Pearlstein, LLC

(57) ABSTRACT

The present invention relates to compositions containing a pterosin compound and derivatives thereof as active ingredients for the prevention or treatment of degenerative brain diseases and, more specifically, to a pharmaceutical composition for the prevention or treatment of degenerative brain diseases and a food composition for the prevention or alleviation of degenerative brain diseases, each of which contains a pterosin compound defined by chemical formula 1 or a derivative thereof as an active ingredient. A method of the present invention can be favorably used to provide a therapeutic agent for preventing or treating degenerative brain diseases, a food for alleviating degenerative brain diseases, or a functional food for the promotion of cognitive functions, by using a pterosin compound extracted from *Pteridium aquilinum* and derivatives thereof.

1 Claim, 18 Drawing Sheets
(11 of 18 Drawing Sheet(s) Filed in Color)

(56) References Cited

OTHER PUBLICATIONS

Skourti-Stathaki, Erini et al., Dissipation of pterosin B in acid soils—Tracking the fate of the bracken fern carcinogen ptaquiloside, Chemosphere, 2016, pp. 453-459, vol. 165, Elsevier.
Uddin, Shaikh J. et al., (2S,3S)-Sulfated Pterosin C, a Cytotoxic Sesquiterpene from the Bangladeshi Mangrove Fern *Acrostichum aureum*, Journal of Natural Products, 2011, pp. 2010-2013, vol. 74, ACS Publications.
Mohammad, Rizgar Hassan et al., Isolation and characterisation of 13 pterosins and pterosides from bracken (*Pteridium aquilinum* (L.) Kuhn) rhizome, Phytochemistry, 2016, pp. 82-94, vol. 128, Elsevier.
Virgilio, Antonella et al., Ptaquiloside, the Major Carcinogen of Bracken Fern, in the Pooled Raw Milk of Healthy Sheep and Goats: An Underestimated, Global Concern of Food Safety, Journal of Agricultural and Food Chemistry, 2015, pp. 4886-4892, vol. 63, ACS Publications.
Sun, Yong et al., Rapid characterization of chemical constituents in Radix Tetrastigma, a functional herbal mixture, before and after metabolism and their antioxidant/antiproliferative activities, Journal of Functional Foods, 2015, pp. 300-318, vol. 18, Elsevier.
Oshiro, Yasuo et al., Novel Cerebroprotective Agents with Central Nervous System Stimulating Activity. 1. Synthesis and Pharmacology of 1-Amino-7-hydroxyindan Derivatives, Journal of Medicinal Chemistry, 1991, pp. 2004-2013, vol. 34, No. 7.
Quermonne, Ma et al., Effective cerebral antihypoxic activity of new aminocyclopentanones, Eur J Med Chem, 1992, pp. 961-965, vol. 27, Elsevier, Paris.

* cited by examiner

FIG. 2

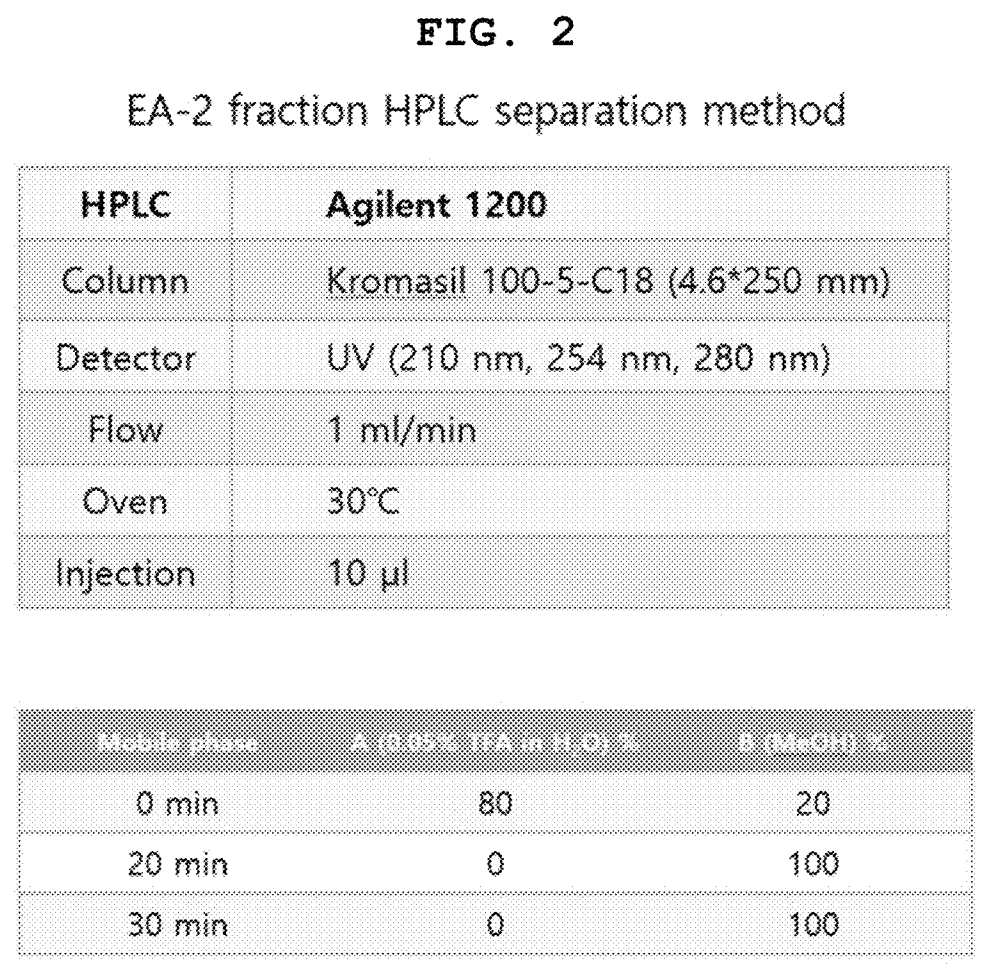

EA-2 fraction HPLC separation method

| HPLC | Agilent 1200 |
| --- | --- |
| Column | Kromasil 100-5-C18 (4.6*250 mm) |
| Detector | UV (210 nm, 254 nm, 280 nm) |
| Flow | 1 ml/min |
| Oven | 30°C |
| Injection | 10 μl |

| Mobile phase | A (0.05% TFA in $H_2O$) % | B (MeOH) % |
| --- | --- | --- |
| 0 min | 80 | 20 |
| 20 min | 0 | 100 |
| 30 min | 0 | 100 |

FIG. 3

| position | 1a | 1b | 1a | 1b |
|---|---|---|---|---|
| | $\delta_H$ mult. ($J$ = Hz) | | $\delta_C$ | |
| 1 | | | 212.9 | 212.7 |
| 2 | 2.43 dt (10.3, 7.0, 2.8) | 2.48 td (7.0, 2.8) | 40.5 | 40.6 |
| 3 | 2.95 ddd (18.2, 6.3, 1.4)<br>2.30 td (18.2, 1.4) | 3.08 ddd (18.2, 7.0, 1.4)<br>2.42[b] | 41.3 | 41.1 |
| 4 | 6.29 brs | 6.28 brs | 127.6 | 126.3 |
| 5 | | | 147.7 | 148.0 |
| 6 | | | 36.4 | 42.6 |
| 7 | | | 206.6 | 207.1 |
| 8 | 6.01 brs | 6.08 brs | 129.7 | 130.4 |
| 9 | | | 168.9 | 170.3 |
| 10 | 1.18 d (7.0) | 1.22 d (7.7) | 16.8 | 16.7 |
| 11 | 2.08 d (1.4) | 2.12 d (0.7) | 26.3 | 20.8 |
| 12 | 1.03 brd (3.5) | 1.06 t (3.5) | 21.3 | 17.93 |
| 13 | 2.58 brd (4.2) | 1.45 q (3.5) | 21.4 | 17.95 |
| 14 | 2.16 s | 2.16 s | 27.36 | 27.38 |

[a]Measured at 700 and 175 MHz; obtained $CDCl_3$ with TMS as an internal standard. [b]Overlapped signal.

FIG. 11
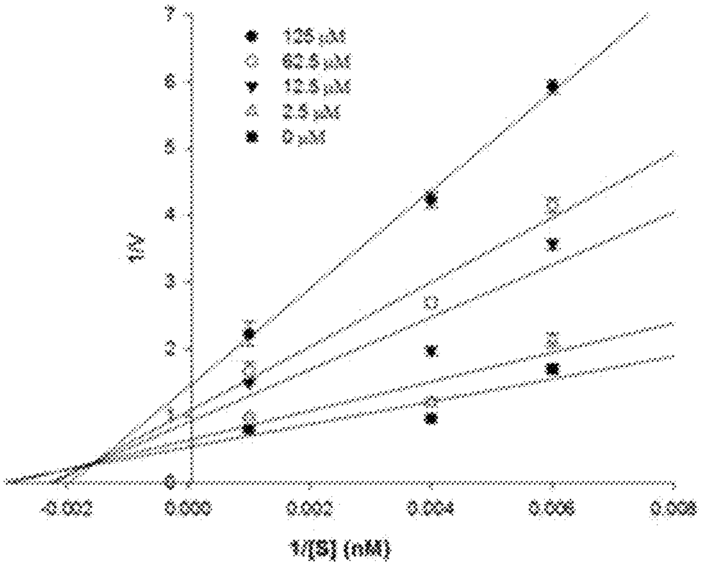
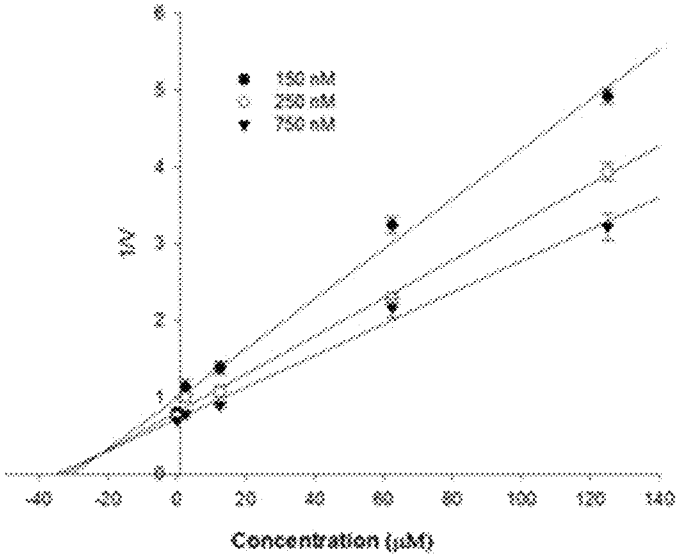
| Test compound | Ki (μM) | Inhibition type |
|---|---|---|
| E2-6 | 19.03 | Mixed-type |

FIG. 12

| Compounds | AutoDock B.E. (kcal/mol) | Hydrogen bonding interactions | Hydrophobic interactions | Other interactions |
|---|---|---|---|---|
| | | BACE1 docking | | |
| QUD | -7.59 | Asp32, Asp228, Gly230 | Leu30, Tyr71, Phe108, Val332 | |
| Quercetin | -5.68 | Ser36, Asn37, Ile126 | Val69, Tyr71, Trp76, Phe108, Arg128 | Val69 (π-sigma) |
| (2*R*,3*R*)-Pteroside C | -6.77 | Gln73, Trp76, Asp228 | Val69, Tyr71, Trp76, Phe108 | |
| | | AChE docking | | |
| E2020 | -10.28 | Phe295 | Trp86, Trp286, Tyr337, Phe338, Tyr341 | Trp286, Tyr341 (π-sigma) |
| Berberine | -8.61 | Phe295, Arg296 | Tyr124, Trp286, Phe297, Phe338, Tyr341 | |
| (2*R*,3*R*)-Pteroside C | -6.85 | Phe295, Gly121, Ser203 | Tyr72, Tyr124, Trp286, Phe338, Tyr341 | |
| | | BChE docking | | |
| 3F9 | -8.49 | | Ile69, Gly116, Trp231, Leu286, Ala328, Phe329, Tyr332 | Asp70 (π-anion) |
| Berberine | -6.67 | Trp82, Gly117 | Trp82, Ala328, Phe329, His438 | |
| (2*R*,3*R*)-Pteroside C | -5.99 | Gly116, Gly117, Pro285 | Trp82, Ala328, Met437, His438, Tyr440 | Trp82 (π-sigma) |

COMPOSITIONS CONTAINING PTEROSIN COMPOUND AND DERIVATIVES THEREOF ACTIVE INGREDIENTS FOR PREVENTION OR TREATMENT OF DEGENERATIVE BRAIN DISEASES

CROSS-REFERENCE TO RELATED APPLICATIONS

This is a National Stage Application of International Patent Application No. PCT/KR2017/011666, filed Oct. 20, 2017, which claims the benefit of and priority to Korean Patent Application No. 10-2017-0076701, filed Jun. 16, 2017 and Korean Patent Application No. 10-2017-0078655, filed Jun. 21, 2017, the contents of which are incorporated fully by reference herein.

TECHNICAL FIELD

The present invention relates to a composition comprising a pterosin compound and a derivative thereof as an active ingredient for preventing or treating degenerative brain disease and, more particularly, to a pharmaceutical composition for preventing or treating a degenerative brain disease and a food composition for prevention or alleviation of degenerative brain disease, each of which contains a pterosin compound defined by Chemical Formula 1 or a derivative thereof as an active ingredient.

BACKGROUND ART

The present application claims the priority benefit of Korean Patent Application Number 10-2017-0076701, filed Jun. 16, 2017 and Korean Patent Application Number 10-2017-0078655, filed Jun. 21, 2017, each of which is incorporated herein in its entirety by reference.

Dementia is a syndrome in which severe impairments in memory, concentration, language, and cognition have progressed over a long period of time due to damage to and loss of nerve cells, ultimately resulting in a loss of mental capacity and social activity. Representative among diseases causative of dementia is Alzheimer's disease. Alzheimer's disease is divided into a sporadic type and a familial type, according to causes thereof and affects 5% of people over 65 years of age and 20% of people over 80 years of age (Launer et al., 1999, In: Iqbal et al., (Eds.) Alzheimer's Disease and related disorders: Etiology, Pathogenesis and Therapeutics, John Wiley & Sons, New York, NY, USA. pp. 9-15). Although being poorly understood for 80-90% of Alzheimer's disease cases, the pathogenic mechanism is generally accounted for by the amyloid hypothesis and cholinergic hypothesis. People with genetic mutations such as presenilin (PS) 1 type and 2 type have 100% rate of onset of Alzheimer's disease before age 65.

According to the amyloid hypothesis, symptoms of Alzheimer's disease are mainly caused by amyloid beta (hereinafter referred to as "Aβ"), which forms senile plaques outside nerve cells of brain tissues, and a hyperphosphorylated tau proteins, which form a paired helical filament inside nerve cells (Querfurth and Laferia, 2010, N Engl J Med, 362:329-344). Aβ denotes peptides of 40-42 amino acids which are formed through APP's amino acid sequence specific metabolism by β- and γ-secretases. Aβ molecules are reported to aggregate by themselves to cause neurotoxicity, synaptic loss, and inflammation (Cappari et al, Neurochem Res, 2008, 33:526-532). Tau proteins are bound to microtubes, functioning to maintain cellular morphology and the skeleton. Hyperphosphorylated tau proteins are separated from microtubules, destroy the microtubules, and form neurofibrillary tangles leading to neuronal death (Iqbal et al, Acta Neuropathol, 2009, Acta Neuropathol, 118(1): 53-69).

Beta secretase (beta-site APP-cleaving enzyme 1), also called BACE (beta-site APP-cleaving enzyme), is the enzyme that plays the most important role in generating amyloid beta. There are two kinds of BACE: BACE-1 and BACE-2. Of them, BACE-1 accounts for most of beta-secretase activity (about 90%) and thus is far more responsible for the generation of amyloid beta (Vassar R., Advanced Drug Delivery Review, 2002, 54:1589-1602). Therefore, substances that selectively inhibit the activity of BACE-1 have been fully recognized to be valuable as a therapeutic agent for Alzheimer-type dementia.

Acetylcholine is a neurotransmitter playing a role in memory and thinking ability and is less common in a specific brain site of a dementia patient (Tricco et al., 2012, Syst Rev, 28:1-31). Therefore, inhibitors of acetylcholinesterase (AChE) and butyrylcholinesterase (BChE) activity have been used to treat dementia (Alzheimer's Association, Alzheimer's Dement, 2012, 8:131-168).

Patients with Alzheimer's disease are reported to amount to about 26 million people worldwide as of 2008 and are expected to grow to more than 100 million by 2050 due to an increase in the elderly population, but the development of fundamental therapeutic agents has progressed very slowly.

Among current drugs on the market are acetylcholinesterase inhibitors (such as Aricept, Exelon, Reminy1, etc.) that maintain a constant concentration of acetylcholine and a NMDA receptor antagonist (Memantine) that inhibits $Ca^{2+}$-associated neuronal cell death. However, these agents are used for the purpose of alleviating the progress of symptoms. There is, therefore, an urgent need for the development of a therapeutic agent that shows a more potent therapeutic effect.

DETAILED DESCRIPTION OF THE INVENTION

Technical Problem

Leading to the present disclosure, intensive research, conducted by the present inventor, into therapy for degenerative brain disease, resulted in the finding that novel pterosin compounds and derivatives thereof are contained in a bracken fern extract and have therapeutic effects on degenerative brain disease by inhibiting the activities of BACE1, AChE, and BChE, as assayed in vivo.

Therefore, an objective of the present disclosure is to provide a pharmaceutical composition comprising a pterosin compound defined by the following Chemical Formula 1 or a derivative thereof as an effective ingredient for preventing or treating a degenerative brain disease:

[Chemical Formula 1]

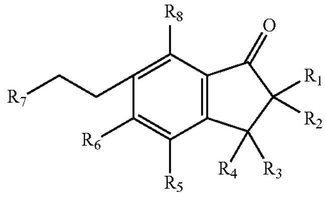

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid (—$SO_3H$), O-cycloalkyl, O-heterocycloalkyl, glucose, and O-glucose.

Another objective of the present disclosure is to provide a method for preparation of the pterosin compound or derivative of claim 1, the method comprising the steps of: (a) soaking a bracken fern in water or an organic solvent of 1 to 4 carbon atoms to obtain an extract; (b) fractionating the extract obtained in step (a) with ethyl acetate; and (c) isolating and purifying the ethyl acetate fraction obtained in step (b) by concentration-gradient chromatography.

Another objective of the present disclosure is to provide a food composition comprising a pterosin compound represented by Chemical Formula 1 or a derivative thereof as an effective ingredient for prevention or alleviation of degenerative brain disease.

Another objective of the present disclosure is to provide a food composition comprising a pterosin compound defined by Chemical Formula 1 or a derivative thereof as an effective ingredient for enhancing cognitive function.

Another objective of the present disclosure is to provide a use of a compound defined by Chemical Formula 1 or a pharmaceutically acceptable salt thereof in preparing an agent for treating a degenerative brain disease.

Another objective of the present disclosure is to provide a method for treatment of degenerative brain disease, the method comprising administering to a subject in need thereof an effective amount of a composition comprising a compound defined by Chemical Formula 1 or a pharmaceutically acceptable salt thereof as an effective ingredient.

Another objective of the present disclosure is to provide a use of a compound defined by Chemical Formula 1 or a salt thereof in preparing an agent for enhancing cognitive function.

Another objective of the present disclosure is to provide a method for enhancing cognitive function, the method comprising administering to a subject in need thereof an effective amount of a composition comprising a compound defined by Chemical Formula 1 or a salt thereof as an effective ingredient.

Another objective of the present disclosure is to provide a novel compound defined by the following Chemical Formula 2:

[Chemical Formula 2]

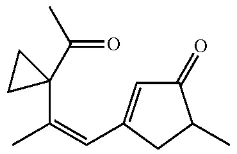

Another objective of the present disclosure is to provide a method for preparation of the novel compound, the method comprising the steps of: (a) soaking a bracken fern in water or an organic solvent of 1 to 4 carbon atoms to obtain an extract; (b) fractionating the extract obtained in step (a) with ethyl acetate; and (c) isolating and purifying the ethyl acetate fraction obtained in step (b) by concentration-gradient chromatography.

Another objective of the present disclosure is to provide a pharmaceutical composition comprising the novel compound defined by the following Chemical Formula 2 or a pharmaceutically acceptable salt thereof as an effective ingredient for preventing or treating degenerative brain disease.

Another objective of the present disclosure is to provide a food composition comprising the novel compound defined by Chemical Formula 2 as an effective ingredient for prevention or alleviation of degenerative brain disease.

Another objective of the present disclosure is to provide a food composition comprising the novel compound defined by Chemical Formula 2 as an effective ingredient for enhancing cognitive function.

Another objective of the present disclosure is to provide a use of the compound defined by Chemical Formula 2 or a pharmaceutically acceptable salt thereof in preparing a therapeutic formulation for degenerative brain disease.

Another objective of the present disclosure is to provide a method for treatment of degenerative brain disease, the method comprising administering to a subject in need thereof an effective amount of a composition comprising the compound defined by Chemical Formula 2 or a pharmaceutically acceptable salt thereof as an effective ingredient.

Another objective of the present disclosure is to provide a use of the compound defined by Chemical Formula 2 or a salt thereof in preparing an agent for enhancing cognitive function.

Another objective of the present disclosure is to provide a method for enhancing cognitive function, the method comprising administering to a subject in need thereof an effective amount of a composition comprising the compound defined by Chemical Formula 2 or a salt thereof as an effective ingredient.

Technical Solution

In order to accomplish the objectives, an aspect of the present disclosure provides a pharmaceutical composition comprising a pterosin compound defined by the following Chemical Formula 1 or a derivative thereof as an effective ingredient for preventing or treating degenerative brain disease:

<Chemical Formula 1>

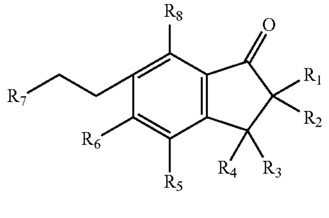

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid (—$SO_3H$), O-cycloalkyl, O-heterocycloalkyl, glucose, and O-glucose.

Another aspect of the present disclosure provides a method for preparation of the pterosin compound or derivative of claim 1, the method comprising the steps of: (a) soaking a bracken fern in water or an organic solvent of 1 to 4 carbon atoms to obtain an extract; (b) fractionating the extract obtained in step (a) with ethyl acetate; and (c) isolating and purifying the ethyl acetate fraction obtained in step (b) by concentration-gradient chromatography.

Another aspect of the present disclosure provides a food composition comprising a pterosin compound defined by Chemical Formula 1 or a derivative thereof as an effective ingredient for prevention or alleviation of degenerative brain disease:

<Chemical Formula 1>

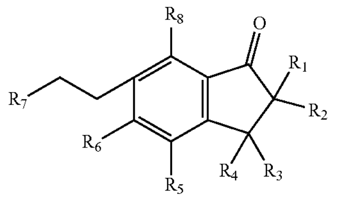

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid (—$SO_3H$), O-cycloalkyl, O-heterocycloalkyl, glucose, and O-glucose.

Another aspect of the present disclosure provides a food composition comprising a pterosin compound defined by Chemical Formula 1 or a derivative thereof as an effective ingredient for enhancing cognitive function:

<Chemical Formula 1>

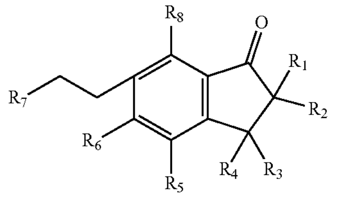

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid (—$SO_3H$), O-cycloalkyl, O-heterocycloalkyl, glucose, and O-glucose.

Another aspect of the present disclosure provides a use of a compound defined by Chemical Formula 1 or a salt thereof in preparing an agent for treatment of degenerative brain disease.

Another aspect of the present disclosure provides a method for treatment of degenerative brain disease, the method comprising administering to a subject in need thereof an effective amount of a composition comprising a compound defined by Chemical Formula 1 or a salt thereof as an effective ingredient.

Another aspect of the present disclosure provides a use of a compound defined by Chemical Formula 1 or a salt thereof in preparing an agent for enhancing cognitive function.

Another aspect of the present disclosure provides a method for enhancing cognitive function, the method comprising administering to a subject in need thereof an effective amount of a composition comprising a compound defined by Chemical Formula 1 or a salt thereof as an effective ingredient.

Another aspect of the present disclosure provides the novel compound defined by the following Chemical Formula 2:

[Chemical Formula 2]

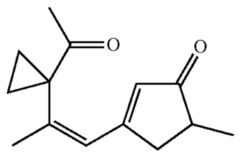

Another aspect of the present disclosure provides a method for preparation of the novel compound, the method comprising the steps of: (a) soaking a bracken fern in water or an organic solvent of 1 to 4 carbon atoms to obtain an extract; (b) fractionating the extract obtained in step (a) with ethyl acetate; and (c) isolating and purifying the ethyl acetate fraction obtained in step (b) by concentration-gradient chromatography.

Another aspect of the present disclosure provides a pharmaceutical composition comprising the novel compound defined by the following Chemical Formula 2 or a pharmaceutically acceptable salt thereof as an effective ingredient for preventing or treating degenerative brain disease.

Another aspect of the present disclosure provides a food composition comprising the novel compound defined by Chemical Formula 2 as an effective ingredient for prevention or alleviation of degenerative brain disease.

Another aspect of the present disclosure provides a food composition comprising the novel compound defined by Chemical Formula 2 as an effective ingredient for enhancing cognitive function.

Another aspect of the present disclosure is to provide a use of the compound defined by Chemical Formula 2 or a pharmaceutically acceptable salt thereof in preparing a therapeutic formulation for degenerative brain disease.

Another aspect of the present disclosure provides a method for treatment of degenerative brain disease, the method comprising administering to a subject in need thereof an effective amount of a composition comprising the compound defined by Chemical Formula 2 or a pharmaceutically acceptable salt thereof as an effective ingredient.

Another aspect of the present disclosure provides a use of the compound defined by Chemical Formula 1 or a salt thereof in preparing an agent for enhancing cognitive function.

Another aspect of the present disclosure provides a method for enhancing cognitive function, the method comprising administering to a subject in need thereof an effective amount of a composition comprising the compound defined by Chemical Formula 2 or a salt thereof as an effective ingredient.

Below, a detailed description will be given of the present disclosure.

The present disclosure provides a pharmaceutical composition comprising a pterosin compound defined by the following Chemical Formula 1 or a derivative thereof as an effective ingredient for preventing or treating a degenerative brain disease:

[Chemical Formula 1]

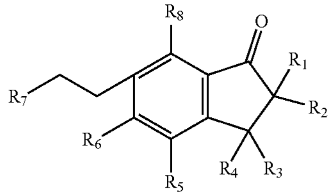

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid ($-SO_3H$), O-cycloalkyl, O-heterocycloalkyl, glucose, and O-glucose.

The term "alkyl", as used herein, is adopted to describe a radical bearing a straight or branched alkyl of 1 to 4 carbon atoms or a part of the radical, examples of which include methyl, ethyl, propyl, isopropyl, n-butyl, isobutyl, and tert-butyl.

The term "alkenyl", as used herein, refers to a straight or branched, mono- or divalent hydrocarbon of 2-10 carbon atoms (e.g., C2-C10) with one or more double bonds therein. Examples of alkenyl include, but are not limited to, ethenyl, propenyl, propenylene, allyl, and 1,4-butadienyl.

The term "alkynyl", as used herein, refers to a straight or branched mono- or divalent hydrocarbon of 2-10 carbon atoms (e.g., C2-C10) with one or more triple bonds therein. Examples of alkynyl include, but are not limited to, ethynyl, ethylene, 1-propynyl, 1-butynyl, 2-butynyl, and 1-methyl-2-butynyl.

As used herein, the term "alcohol" is adopted to describe a straight or branched alcohol or alkoxy radical of 1 to 4 carbon atoms. Examples of the radical include methanol, ethanol, propanol, butanol, and alkoxy radicals thereof. Examples of the alkoxy radical include methoxy, ethoxy, isopropoxy, and tert-butoxy.

As used herein, the term "halogen" refers to an element in the halogen Group as exemplified by fluorine, chlorine, bromine, and iodine. In the present disclosure, $R_7$ may be preferably chlorine.

The pterosin compounds of the present disclosure or derivatives thereof are sesquiterpenoids found in bracken fern and are characterized in that they are purified from bracken fern extracts. Examples of the pterosin compound of the present disclosure or a derivative thereof include, but are not limited to, pterosin A, pterosin B, pterosin C, pterosin D, pterosin J, pterosin M, pterosin P, pterosin S, pterosin Z, pteroside A, pteroside $A_2$, pteroside B, pteroside C, pteroside D, pteroside N, pteroside P, pteroside Z, and sulfated pterosin C.

In addition, the pterosin compound of the present disclosure may have a non-aromatic double bond and at least one asymmetric center and may exist as a racemate or racemic mixture, a single enantiomer, an individual diastereomer, a diastereomer mixture, or a cis- or trans-isomer or in the form of all of the isomers, with preference for a cis- or trans-isomer.

For example, pterosin C may be one of the isomers (2R, 3S)-pterosin C, (2S, 3S)-pterosin C, (2R, 3R)-pterosin C, and (2S, 3R)-pterosin C.

Pteroside C may take the isomeric form of (2S, 3R)-pteroside C or (2R, 3R)-pteroside C.

Sulfonated pterosin C may be in the form of (2R, 3S)-sulfonated pterosin C or (2S, 3S)-sulfonated pterosin C.

The pterosin compound or a derivative thereof according to the present disclosure may be separated from a natural resource or may be prepared by a chemical synthesis method, known in the art, for novel compounds.

Preferably, the pterosin compound of the present disclosure or a derivative thereof can be isolated and purified from a natural plant. That is, the compound or derivative can be obtained from an entire plant or a part thereof, using a conventional method for extraction and isolation of a substance. In order to acquire a desired extract, stems, roots, or leaves may be appropriately dried and macerated in water or a suitable organic solvent. A desired extract may be purified using a purification method known to those skilled in the art. Preferably, the pterosin compound or derivative of the present invention may be isolated and purified form bracken fern.

By way of example, the bracken fern may be plants in the family Dennstaedtiaceae or Pteridaceae. Non-limitative examples of the plants include *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiate*, and *Pteris ensiformi*. These plants live worldwide and can be easily found particularly in Wulai Township, Taipei County, Mountain Datun, and Taipei City.

The pterosin compound of the present disclosure and a derivative thereof can be isolated and purified by a method comprising the following steps of:

(a) soaking a bracken fern in water or an organic solvent of organic solvent of 1 to 4 carbon atoms to obtain an extract;

(b) fractionating the extract of step (a) with ethyl acetate or butanol; and (C) isolating and purifying an ethyl acetate fraction or butanol fraction by concentration-gradient chromatography.

In step (a), the bracken fern may be used as the whole entity or in a dried form. The extraction yield may be improved with a pulverized bracken fern which may be obtained by grinding a dried bracken fern body in a grinder. For the dried bracken fern, any method of drying under the sun, drying in the shade, hot-wind drying, lyophilization, and natural drying may be used, with preference for hot-wind drying and lyophilization.

The organic solvent of 1 to 4 carbon atoms for use in soaking an extract out of bracken ferns may be methanol, ethanol, propanol, isopropanol, butanol, acetone, ether, chloroform, ethyl acetate, methylene chloride, hexane, cyclohexane, dichloromethane, or petroleum ether. In one embodiment of the present disclosure, bracken ferns are soaked in water.

In step (b), the extract obtained in step (a) is fractionated. In this regard, the distribution and extraction is carried out with ethyl acetate or butanol.

The ethyl acetate fraction or butanol fraction obtained in step (b) is separated using concentration-gradient chromatography. In the context of the chromatography, column chromatography with various synthetic resins, such as silica gel, active alumina, or the like loaded into the column, and high-performance liquid chromatography (HPLC) may be used alone or in combination. Preferably, the ethyl acetate fraction or the butanol fraction obtained in step (b) may be loaded into a silica gel column from which various fractions are then eluted while gradually increasing the polarity of the eluent by adjusting the composition of the eluent. Of the fractions in the above process, an active fraction may be subjected again to concentration-gradient silica gel chromatography in which the polarity of the eluent is gradually increased by adjusting the composition of the eluent. However, the extraction and isolation of the compound is not limited to the above-mentioned method.

In step (c), the ethyl acetate fraction or the butanol fraction obtained in step (b) is isolated and purified by concentration-gradient chromatography.

In the context of the chromatography, column chromatography with various synthetic resins, such as silica gel, active alumina, or the like loaded into the column, and high-performance liquid chromatography (HPLC) may be used alone or in combination. Preferably, the novel compound may be isolated or purified using high-performance liquid chromatography.

Methods available for isolating the compounds are well known in the art. For example, reference may be made to [Takahashi et al, Phytother. Res, 2004, 18, 573, Sheridan et al, Planta Med., 1999, 65, 271, Nagao et al., Mutation Research, 1989, 215, 173, Murakami et al., Chem. Pharm. Bull, 1976, 24, 2241, and Kuraishi et al., Chem. Pharm. Bull, 1985, 33, 2305]. The compounds may also be synthesized by chemical synthesis methods. Non-naturally occurring pterosin compounds may be converted from naturally occurring compounds (for example, see [Banerji et al, Tetrahedron Letters, 1974, 15, 1369, Hayashi et al., Tetrahedron Letters, 1991, 33, 2509, and McMorris et al., J. Org. Chem., 1992, 57, 6876]) or may be newly synthesized using methods known in the art.

Methods, useful for the synthesis of the pterosin compound, for synthetic chemical conversion and protection groups (protection and deprotection) are known in the art. For example, reference may be made to [R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof].

In one embodiment of the present disclosure, 200-500 g of bracken fern was soaked in hot water and the resulting hydrothermal extract was added to and well mixed with ethyl acetate (EA). Then, the ethyl acetate fraction was dissolved in DMSO and diluted in water before application to column chromatography to give seven fractions. The fractions were analyzed by HPLC to extract the novel compound and compounds of Chemical Formula 1 (see Example 1 and FIGS. 1 to 3). Separately, the hydrothermal extract was added to and well mixed with butanol. The resulting butanol fraction was dissolved in DMSO and then diluted in water before application to column chromatography to give nine fractions. These fractions were analyzed by HPLC to extract the compounds of the present disclosure (see Example 1 and FIGS. 1 to 3).

Degenerative brain disease causes various symptoms with the generation of a degenerative change in neurons of the central nervous system. In most cases, because the disease is slowly developed since the onset thereof, patients have lived normally for a long period of time from their birth before suffering from symptoms. In addition, once occurring, degenerative brain disease gradually progresses over years or decades until the death of the patients. In the most part, the patients have a family history of the disease.

Examples of the degenerative brain disease of the present disclosure include, but are not limited to, Parkinson's disease, Huntington's disease, Alzheimer's disease, mild cognitive impairment, senile dementia and amyotrophic lateral sclerosis, spinocerebellar atrophy, Tourette's syndrome, Friedrich's Ataxia, Machado-Joseph's disease, Lewy body dementia, dystonia, progressive supranuclear palsy, and frontotemporal dementia.

The prevention, treatment, or alleviation of degenerative brain disease is intended to prevent, treat, or alleviate symptoms of the disease. Such symptoms include:

a) Behavioral symptoms such as sleep disturbances, delirium (including fluctuations), aggression, and agitation;
b) Psychological symptoms such as hallucinations, delusions, anxiety, and depression;
c) Motor symptoms which mean impaired ability to carry out motor activities despite intact motor function; and
d) Learning and cognitive impairment, for example, impaired ability to learn new information or to recall previously learned information (e.g., impaired social memory), aphasia, apraxia, agnosia, disturbance in executive functioning, etc.

The pharmaceutical composition comprising the pterosin compound or a derivative thereof according to the present disclosure may be formulated, alone or in combination with a pharmaceutically acceptable carrier, into a suitable form and may further comprise an excipient or a diluent. As used herein, the term "pharmaceutically acceptable" means pertaining to being physiologically acceptable and non-toxic so as not to invoke allergic responses, such as gastric disturbance, dizziness, and similar reactions when an ingredient relevant thereto is administered to a human.

The pharmaceutically acceptable carrier may be for use in oral or parenteral administration. Examples of carriers for oral administration include lactose, starch, cellulose derivatives, magnesium stearate, and stearic acid. In addition, various oral substances used in the drug delivery of peptide agents may be available in the present disclosure. As carriers for parenteral administration, water, suitable oil, a saline solution, aqueous glucose, and glycol may be used. A stabilizer and a preservative may additionally be used in the present disclosure. Antioxidants, such as sodium bisulphite, sodium sulphite and ascorbic acid, can be suitably used as stabilizers. Benzalkonium chloride, methyl- or propyl-paraben, and chlorobutanol fall within the scope of suitable preservatives. The pharmaceutical composition of the present disclosure may further comprise a lubricant, a humectant, a sweetener, a flavorant, an emulsifier, a suspending agent, and so forth in addition to the ingredients mentioned above. For other pharmaceutically acceptable carriers and formulations, reference may be made to Remington's Pharmaceutical Sciences, 19th ed., Mack Publishing Company, Easton, Pa., 1995.

The composition of the present disclosure may be administered to mammals including humans in any manner. For example, the composition can be administered orally or parenterally. Examples of parenteral administration include, but are not limited to, administration through intravenous, intramuscular, intra-arterial, intramedullary, intrathecal, intracardiac, transdermal, subcutaneous, intraperitoneal, intranasal, intraintestinal, topical, sublingual, and intrarectal routes.

The pharmaceutical composition of the present disclosure may be formulated into preparations for oral or parenteral administration according to the administration routes as described above.

For oral dosage forms, the composition of the present disclosure was prepared into powders, granules, tablets, pills, sugar-coated tablets, capsules, solutions, gels, syrups, slurries, suspensions and the like, using methods known in the art. For example, an oral preparation can be obtained by combining the active ingredient with a solid excipient, followed by pulverizing, mixing, adding suitable auxiliaries, and then processing the mixture into a granulated mixture as a tablet or sugar-coated tablet. Examples of suitable excipients include saccharides such as lactose, dextrose, sucrose, sorbitol, mannitol, xylitol, erythritol, and maltitol; starches such as corn starch, wheat starch, rice starch and potato starch; celluloses such as cellulose, methyl cellulose, sodium carboxymethyl cellulose and hydroxypropyl methyl cellulose; and fillers such as gelatin, polyvinylpyrrolidone, etc. Optionally, crosslinked polyvinylpyrrolidone, agar, alginic acid or sodium alginate may be added as a disintegrant. Furthermore, the pharmaceutical composition of the present disclosure may further comprise an anti-coagulant, a lubricant, a humectant, a flavorant, an emulsifier, and a preservative.

For parenteral dosage forms, the composition may be formulated into an injection, a cream, a lotion, an external ointment, an oil, a moisturizer, a gel, an aerosol, and a nasal inhalant. As for all of the dosage forms, reference may be made to documents well known in the pharmaceutical chemistry field such as Remington's Pharmaceutical Science, 19th ed., Mack Publishing Company, Easton, PA, 1995.

The total effective amount of the composition according to the present disclosure may be administered to a patient in a single dose or in multiple doses for a long period of time with a fractionated treatment protocol. The pharmaceutical composition of the present disclosure may contain variable amounts of the effective ingredient depending on the disease severity. The total amount of the effective ingredient in the pharmaceutical composition of the present disclosure generally ranges from about 0.01 to 10,000 mg/kg body weight/day, or in some embodiments, from 0.1 to 500 mg/kg body weight/day. However, the dose of the pharmaceutical composition may be suitably determined by considering various factors, such as age, body weight, health condition, sex, disease severity, diet, and excretion of a subject in need of treatment, as well as administration frequency and administration route. When those factors are considered, the skilled person in the art may determine the appropriate dose of the composition of the present disclosure. The pharmaceutical composition is not limited in terms of types of formulation, administration routes, and administration methods, as long as it possesses the effectiveness according to the present disclosure.

According to the present disclosure, the pterosin compound defined by Chemical Formula 1 or a derivative thereof may be provided in the form of a food composition for preventing or alleviating a degenerative brain disease or for enhancing a cognitive function.

The pterosin compound and the degenerative brain disease are as described above.

As used herein, the term "cognition" refers to all the processes in which the brain accepts and stores information and retrieves and utilizes stored information, including thinking, speaking, remembering, judging, and acting processes carried out in daily life. The term "cognitive function" means the ability of the brain to take and store information and to retrieve and use stored information, including memory, thought, judgement, and execution performances. Such cognitive functions can be broadly classified into attention, language, time and space, memory, and execution (or management) functions. The cognitive function of the present disclosure includes learning, memory, or concentration.

The food composition comprising the pterosin compound or a derivative thereof according to the present disclosure may be in any form, including functional foods, nutritional supplements, health foods, and food additives. The food composition can be prepared into various forms according to conventional methods known in the art.

For example, the food composition of the present disclosure may be prepared into a tea, juice, or beverage, or into granules, capsule, or powder as a health food. Also, the food composition of the present disclosure may be mixed with a substance or active ingredient known to have an effect of body fat reduction, cholesterol level reduction, or hypertension.

For functional foods, the food composition of the present disclosure may be also added to drinks (including alcoholic drinks), fruits and processed products thereof (e.g., canned fruit, bottled fruit, jam, marmalade), fish, meat, and processed products thereof (e.g., ham, sausage, corned beef), confectionery and noodles (e.g., udon, buckwheat noodles, ramen, spaghetti, macaroni), fruit juice, beverages, cookies, Korean taffy, dairy products (e.g., butter, cheese), vegetable oils, margarine, vegetable proteins, retort foods, frozen foods, seasonings (e.g., soybean paste, soy sauce, sauce), or the like.

The food composition according to the present disclosure is preferably contained in an amount of 0.01-50 wt. % of the total weight of the food finally produced, with no limitations thereto. For use as a food additive, the food composition of the present disclosure may be prepared into the form of powder or concentrated liquid.

Like general beverages, in addition, the food composition of the present invention may contain various flavors, natural carbohydrates, and the like as additional components. The carbohydrates are monosaccharides such as glucose, fructose, and the like; disaccharides such as maltose and sucrose; polysaccharides such as dextrin and cyclodextrin; and sugar alcohols such as xylitol, sorbitol, erythritol, and the like. Sweeteners including natural sweeteners such as taumartin, stevia extract, etc. and synthetic sweeteners such as saccharin, aspartame, and the like can be used. The ratio of the natural carbohydrate is generally about 0.01-0.04 g and preferably about 0.02-0.03 g per 100 mL of the composition of the present disclosure, but is not limited thereto.

The definition of such terms as excipient, binder, disintegrant, lubricant, tasty acid, fragrance, and so forth is described in literatures known in the art and encompasses those with the same or similar functions (Korean Pharmacopoeia, Explanation, Moonsung Pub., Korea college of pharmacy conference, $5^{th}$ Ed., p 33-48, 1989).

In addition, the present disclosure provides a use of a compound defined by Chemical Formula 1 or a pharmaceutically acceptable salt thereof in preparing a therapeutic agent for degenerative brain disease.

Furthermore, the present disclosure provides a method for treating a degenerative brain disease in a subject, the method comprising administering, to the subject in need thereof, an effective amount of a composition comprising a compound defined by Chemical Formula 1 or a pharmaceutically acceptable salt thereof as an effective ingredient.

Also, the present disclosure provides a use of a compound defined by Chemical Formula 1 or a pharmaceutically acceptable salt thereof in preparing a cognitive function-enhancing agent.

Also, the present disclosure provides a method for enhancing a cognitive function in a subject, the method comprising administering, to the subject in need thereof, an effective amount of a composition comprising a compound defined by Chemical Formula 1 or a pharmaceutically acceptable salt thereof as an effective ingredient.

As used herein, the term "effective amount" refers to an amount that allows for an improvement in cognitive function or the alleviation, treatment, prevention, detection, or diagnosis of degenerative brain disease when administered to a subject. The term "subject" refers to an animal, preferably, a mammal, and especially, an animal including a human being, and may be a cell, tissue, and organ, or the like originating from an animal. The subject may be a patient in need of such effects.

The term "treatment" or "treating", as used herein, comprehensively refers to alleviating degenerative brain diseases or degenerative brain disease-related diseases or symptoms of degenerative brain diseases or degenerative brain disease-related diseases and is intended to encompass substantially curing, preventing, or reducing the condition of the diseases. What is meant by the term includes alleviating, curing, or preventing one or most of symptoms resulting from degenerative brain disease or degenerative brain disease-related diseases, but is not limited thereto.

As used herein, the term "enhancing" in association with cognitive function refers comprehensively to an enhancing cognitive function and is intended to encompass improvements in cognitive function-related abilities, preferably learning, memory, or concentration. What is meant by the term includes alleviating, curing, or reversing the symptoms such as degenerative brain disease-caused weakness and degradation of cognitive functions, but is not limited thereto.

In addition, the present disclosure provides the novel compound defined by the following Chemical Formula 2:

[Chemical Formula 2]

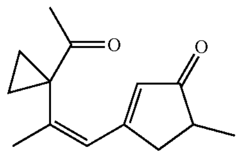

The novel compound of Chemical Formula 2 was first identified by the present inventor, which is well explained in the Example section of the specification.

The novel compound is 3-[2-(1-acetylcyclopropyl)-1-propenyl]-5-methyl-2-cyclopenten-1-one (3-[2-(1-acetylcycloproply)-1-propenyl]-5-methyl-2-cyclopenten-1-one) with a molecular weight of 218.30.

The novel compound may have a non-aromatic double bond and at least one asymmetric center and may exist as a racemate or racemic mixture, a single enantiomer, an individual diastereomer, a diastereomer mixture, or a cis- or trans-isomer or in the form of all of the isomers. All of these isomers are contemplated in the present disclosure.

Contemplated in the present disclosure are also hydrates of the novel compound defined by Chemical Formula 2 or derivatives thereof such as glycosides having compounds, such as glucose, conjugated to the side chains thereof.

The novel compound according to the present disclosure may be separated from a natural resource or may be prepared by a chemical synthesis method, known in the art, for novel compounds.

Preferably, the novel compound of the present disclosure can be isolated and purified from a natural plant. That is, the compound can be obtained from an entire plant or a part thereof, using a conventional method for extraction and isolation of a substance. In order to acquire a desired extract, stems, roots, or leaves may be appropriately dried and macerated in water or a suitable organic solvent. A desired extract may be purified using a purification method known to those skilled in the art. Preferably, the novel compound of the present invention may be isolated and purified form bracken fern.

By way of example, the bracken fern may be plants in the family Dennstaedtiaceae or Pteridaceae. Non-limitative examples of the plants include *Dennstaedtia scandens, Histiopteris incisa, Microlepia speluncae, Pteridium aquilinum* var. *latiusculum, Pteridium revolutum, Hypolepis punctata, Ceratopteris thalictroides, Pteris fauriei, Pteris dimidiate*, and *Pteris ensiformi*. These plants live worldwide and can be easily found particularly in Wulai Township, Taipei County, Mountain Datun, and Taipei City.

The novel compound of the present disclosure can be isolated and purified by a method comprising the following steps of:

(a) soaking a bracken fern in water or an organic solvent of organic solvent of 1 to 4 carbon atoms to obtain an extract;

(b) fractionating the extract of step (a) with ethyl acetate; and (C) isolating and purifying the ethyl acetate fraction by concentration-gradient chromatography.

In step (a), the bracken fern may be used as the whole entity or in a dried form. The extraction yield may be improved with a pulverized bracken fern which may be obtained by grinding a dried bracken fern body in a grinder. For the dried bracken fern, any method of drying under the sun, drying in the shade, hot-wind drying, lyophilization, and natural drying may be used, with preference for hot-wind drying and lyophilization.

The organic solvent of 1 to 4 carbon atoms for use in soaking an extract out of bracken ferns may be methanol, ethanol, propanol, isopropanol, butanol, acetone, ether, chloroform, ethyl acetate, methylene chloride, hexane, cyclohexane, dichloromethane, or petroleum ether. In one embodiment of the present disclosure, bracken ferns are soaked in water.

In step (b), the extract obtained in step (a) is fractionated. In this regard, the distribution and extraction is carried out with ethyl acetate. The ethyl acetate fraction obtained in step (b) is separated using concentration-gradient chromatography. In the context of the chromatography, column chromatography with various synthetic resins, such as silica gel, active alumina, or the like loaded into the column, and high-performance liquid chromatography (HPLC) may be used alone or in combination. Preferably, the ethyl acetate fraction or the butanol fraction obtained in step (b) may be loaded into a silica gel column from which various fractions are then eluted while gradually increasing the polarity of the eluent by adjusting the composition of the eluent. Of the fractions in the above process, an active fraction may be subjected again to concentration-gradient silica gel chromatography in which the polarity of the eluent is gradually increased by adjusting the composition of the eluent. However, the extraction and isolation of the compound is not limited to the above-mentioned method.

In step (c), the ethyl acetate fraction obtained in step (b) is isolated and purified by concentration-gradient chromatography.

In the context of the chromatography, column chromatography with various synthetic resins, such as silica gel, active alumina, or the like loaded into the column, and high-performance liquid chromatography (HPLC) may be used alone or in combination. Preferably, the novel compound may be isolated or purified using high-performance liquid chromatography.

The novel compound defined by Chemical Formula 2 according to the present disclosure is provided for preventing or alleviating degenerative brain disease or for enhancing a cognitive function.

In addition, the present disclosure provides a use of the novel compound defined by Chemical Formula 2 in preparing a therapeutic agent for degenerative brain disease.

Furthermore, the present disclosure provides a method for treatment of degenerative brain disease, the method comprising administering, to a subject in need thereof, an effective amount of a composition comprising a compound defined by Chemical Formula 2 or a pharmaceutically acceptable salt thereof as an effective ingredient.

Also, the present disclosure provides a use of the compound defined by Chemical Formula 2 or a pharmaceutically acceptable salt thereof in preparing a cognitive function-enhancing agent.

Also, the present disclosure provides a method for enhancing a cognitive function, the method comprising administering, to a subject in need thereof, an effective amount of a composition comprising a compound defined by Chemical Formula 2 or a pharmaceutically acceptable salt thereof as an effective ingredient.

The novel compound defined by Chemical Formula 2, degenerative brain disease, and cognitive functions are as described above.

As used herein, the term “effective amount” refers to an amount that allows for an improvement in cognitive function or the alleviation, treatment, prevention, detection, or diagnosis of degenerative brain disease when administered to a subject. The term “subject” refers to an animal, preferably, a mammal, and especially, an animal including a human being, and may be a cell, tissue, and organ, or the like originating from an animal. The subject may be a patient in need of such effects.

The term “treatment”, as used herein, comprehensively refers to alleviating degenerative brain disease or degenerative brain disease-related diseases or symptoms of degenerative brain disease or degenerative brain disease-related diseases and is intended to encompass substantially curing, preventing, or reducing the condition of the diseases. What is meant by the term includes alleviating, curing, or preventing one or most of symptoms resulting from degenerative brain disease or degenerative brain disease-related diseases, but is not limited thereto.

As used herein, the term “enhancing” in association with cognitive function refers comprehensively to an improvement of a cognitive function and is intended to encompass improvements in cognitive function-related abilities, preferably learning, memory, or concentration. What is meant by the term includes alleviating, curing, or reversing the symptoms such as degenerative brain disease-caused weakness and degradation of cognitive functions, but is not limited thereto.

In one embodiment of the present disclosure, the normal NIH3T3 cells and the cancerous B16F10 cells were separately seeded into 96-well plates and incubated in the presence of the compound of Chemical Formula 2. After MTT treatment, absorbance was read at 550 nm using a microplate reader. Based on the measurements, $LD_{50}$ values were calculated. As a result, the compound of Chemical Formula 2 was identified to be non-toxic to the normal cells, but slightly toxic to the cancerous cells.

In another embodiment, examination was made to the effect of the compound of Chemical Formula 2 on the activity of BACE1. In this regard, the compound was applied to the BACE1 enzyme and measured for $IC_{50}$ values with the aid of a BACE1 kit. The compounds were each observed to inhibit the activity of BACE1 in a dose-dependent manner (see Table 3 and FIG. 7)

In another embodiment of the present disclosure, the effect of the compound of Chemical Formula 2 on the activity of cholinesterase was examined by treating acetylcholinesterase (AChE) and butyrylcholinesterase (BChE) with the compound and measuring activities of AChE and BChE to determine $IC_{50}$ values. The compound was identified to inhibit activities of AChE and BChE (see Table 4).

Advantageous Effect

Therefore, the present disclosure provides a composition comprising a pterosin compound and a derivative thereof for prevention, alleviation, or treatment of degenerative brain disease. By the method of the present disclosure, the pterosin compounds extracted from bracken ferns or derivatives thereof can be advantageously used to provide a therapeutic agent for preventing or treating degenerative brain disease or a functional food for alleviating degenerative brain disease or for enhancing a cognitive function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows HPLC conditions for isolating single compounds from EA-2 and butanol fractions.

FIG. 3 shows NMR analysis data for the novel compound.

FIG. 11 shows BACE1 activity inhibition mechanisms and Ki values of the novel compound (Compound 2) as evaluated by Lineweaver plots (X-axis: 1/substrate concentration, Y-axis: 1/initial reaction rate of enzyme) (upper panels) and Dixon plots (X-axis: concentration of the novel compound, Y-axis: 1/initial reaction rate of enzyme) (lower panels).

FIG. 12 is a table in which data of molecular docking simulations of Compound 16 and the positive controls quercetin and berberine for BACE1, AChE, and BChE are summarized, showing bonding energies and binding sites between each compound and the enzymes.

MODE FOR CARRYING OUT THE INVENTION

Figure 1:
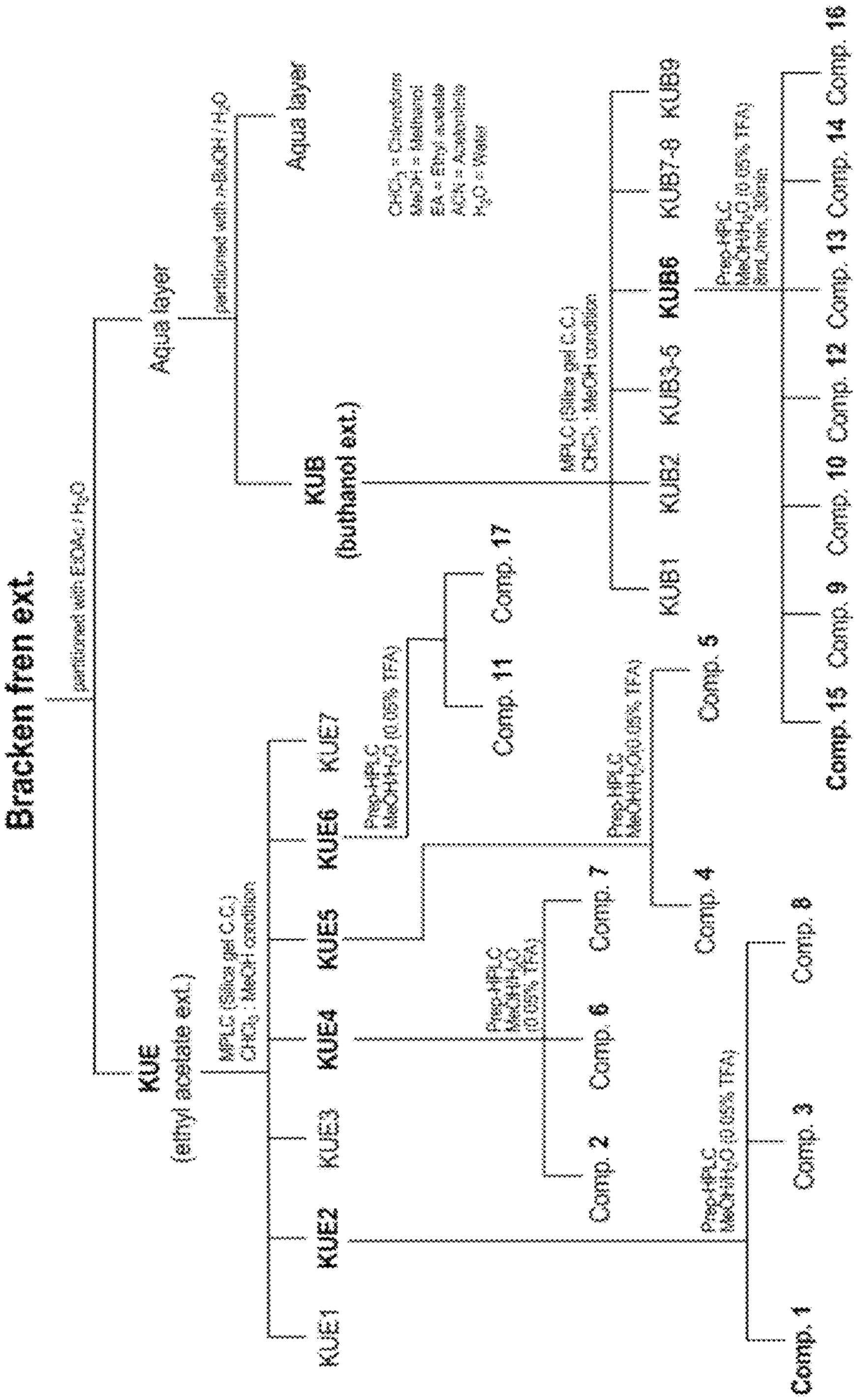
FIG. 1 is a schematic view illustrating processes of isolating and purifying the compounds of the present disclosure and derivatives thereof.
Figure 4:
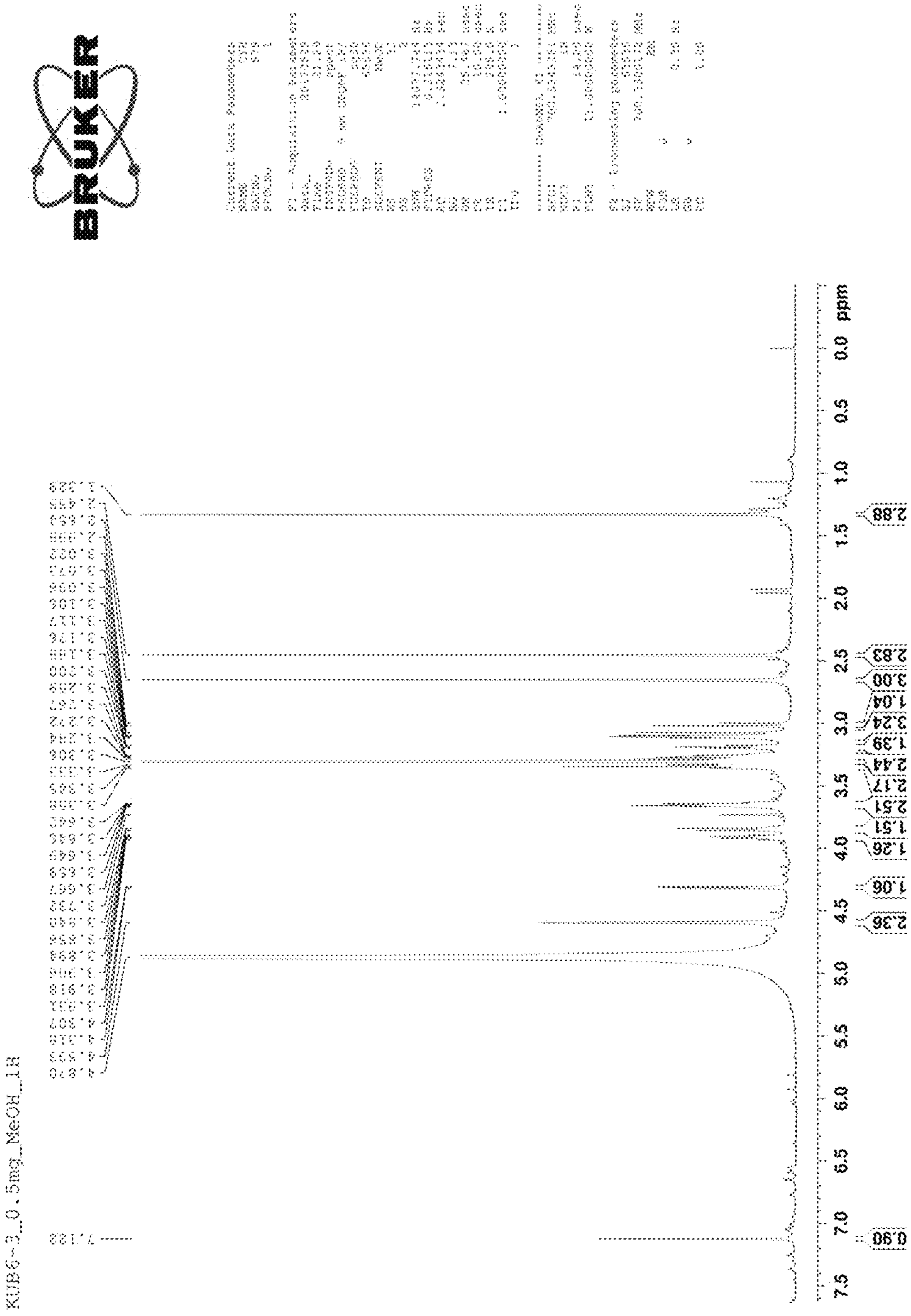
FIG. 4 shows a $^{1}$H-NMR spectrum for pteroside N (Compound 18, comp.15).

Hereinafter, the present invention will be described in detail.

However, the following Examples are set forth to illustrate, but not to limit the present invention.

Experimental Methods

Experimental Instruments $^{1}$H NMR and $^{13}$C NMR spectra were obtained at 700 MHz for $^{1}$H NMR and at 175 MHz for $^{13}$C NMR by Bruker Ascend III 700 spectrophotometer (Bruker Biospin, Rheinstetten, Germany) using deuterium chloroform ($CDCl_3$), methanol ($CD_3OD$), and dimethyl sulfoxide (DMSO-dd.

Column chromatography was performed with silica gel (70-230 meshes; Merk, Darmstadt, Germany) using RP-18 (40-63 mm; Merck) and Sephadex LH-20(20-100 mm; Sigma, St. Louis, MO, USA). Thin layer chromatography (TLC) was performed with pre-coated Kiesel gel 60 F254 plates (0.25 mm; Merck) and 25 RP-18 F 254s plate (5-10 cm, Merk). A spray reagent was 50% $H_2SO_4$. All the chemicals and solvents used in column chromatography were of reagent grade and were used as received without further purification.

Reagents

Electric eel acetylcholinesterase (AChE, EC3.1.1.7), horse serum butyrylcholinesterase (BChE, EC3.1.1.8), acetyl thiocholine iodide (ACh), butyryl thiocholine chloride (BCh), 5,5'-dithiobis) [2-nitrobenzoic acid)](DTNB), quercetin, and berberine were purchased from Sigma-Aldrich Co. (St. Louis, MO, USA). BACE1 (beta-secretase) FRET assay kit was purchased from Pan Vera Co. (Madison, WI, USA). All the chemicals and solvents used in column chromatography were of reagent grade and were used as received without further purification.

MTT Assay

Mouse fibroblast cell line NIH3T3 and mouse melanoma cell line B16F10 were separately seeded at a density of $1\times10^3$ cells/well into 96-well plates and grown in DMEM supplemented with 10% FBS (fetal bovine serum) at 37° C. in a 5% $CO_2$ atmosphere. The cells in each cell were incubated for 24 hours with predetermined concentrations of each of the compounds (pterosin A, pterosin B, pterosin C, pterosin D, pterosin P, pterosin Z, pteroside A, pteroside $A_2$, pteroside B, pteroside C isomers, pteroside D, pteroside N, pteroside P, and pteroside Z) and then for 2 hours with 100 μL of MTT (0.5 mg/ml PBS). After aspiration of the medium from each well, incubation was conducted for 10 min with 100 μL of DMSO. Absorbance at 570 nm was read using a microplate reader (SPECTRA MAX 340PC, Molecular Devices, USA). Absorbance is an index accounting for a number of viable cells and was used to calculate cell proliferation rates according to the following formula. All experiments were conducted three times for reproducibility.

$$\text{Cell proliferation rate (\%)} = OD_{550}(\text{sample})/OD_{550}(\text{control})$$

In Vitro BACE1 Activity Assay

A BACE1 fluorescence resonance energy transfer (FRET) assay kit (β-secretase, recombinant human enzyme) was purchased from Pan Vera Co. (Madison, WI, USA). The assay was carried out according to the manual provided, with a modification made thereto as described by Jung et al. (Jung et al., Biol Pharm Bull, 2010, 33:267-272). Quercetin was used as a positive control.

In Vitro Cholinesterase Activity Assay

Inhibitory activity of the compounds against cholinesterases were assayed using the spectrophotometry developed by Elman et al. (Elman et al., Biochem Pharmcol, 1961, 7:88-95), with ACh and BCh serving as substrates. A reaction mixture in which 140 μL of sodium phosphate buffer (pH 8.0), 20 μL of a test sample solution (final concentration 125 μM), and 20 μL of AChE or BChE were mixed was incubated at room temperature for 15 min. All of the test samples and the positive control (berberine) were dissolved in 10% ethanol in analysis grade. The reaction started with the addition of 10 μL of DTNB and 10 μL of Ach or Bch.

The hydrolysis of Ach or BCh was analyzed using a microplate spectrophotometer (Molecular Devices, Inc., Sunnyvale, CA, USA) at 412 nm for 15 min. Briefly, the basis for this assay is the hydrolysis of acetylthiocholine by acetylcholinesterase, producing thiocholine that reacts with DTNB. In this case, peak absorption of the thionitrobenzoate (yellow) produced was detected at 412 nm UV in 96-well microplates so as to measure enzyme activity. Degrees of inhibition were calculated according to 1≤S/E≤100 wherein E and S represent enzyme activities in the presence and absence of a test sample, respectively.

Molecular Docking

In order to examine the inhibitory activity of the compounds of the present disclosure against enzymes, molecular docking study was performed on BACE1, AChE, and BChE. 2-Amino-3-(1r)-1-cyclohexyl-2-[(cyclohexylcarbonyl) amino]ethyl-6-phenoxyquinazolin-3-ium (QUD) was allowed to combine with an X-ray crystal structure of human BACE1 to form a complex. Complexes were formed by combination between ChE and donepezil (E2020) (PDB code: 4EY7) and between BChE and N-[(3R)-1-(2,3-dihydro-1H-inden-2-yl)piperidin-3-yl]methyl-N-(2-methoxyethyl) naphthalene-2-carboxamide (3F9) (PDB code: 4TPK). The complexes thus formed were searched for in the RCSB Protein Databank (https://www.rcsb.org/). Discovery Studio 2017 R2 (BIOVIA, San Diego: Dassault Syst) was used to construct 3D structures of docked ligands in minimal energies.

Docking studies were carried out using Dock AutoDock 4.2.6 software. In order to evaluate molecular docking settings, re-docking experiments were performed for co-crystallized ligands of above-mentioned PDBs. Thereafter, confirmed docking protocols were applied to the docking of other compounds. In the docking process, the receptor protein was set as a rigid while the ligand was set in a completely flexible state. Prior to docking, protein and ligand structures were processed using AutoDock Tools (ADT) 1.5.6. Co-crystallized ligand and water molecules were removed from the original PDB file. Kollman and Gasteiger charges united with polar hydrogen atom were assigned for protein structures. For docking calculation, Gasteiger charges were added to the ligands.

The number of rotatable bonds was set and all torsions could be rotated. A grid box for covering a protein active site for the co-crystallized ligand was setup for the AutoGrid program. The grid of 40×40×40 Å$^3$, with a spacing of 0.375 Å was centered on the co-crystallized ligand of each enzyme. Lamarckian genetic Algorithm (LGA) was used for searching for structures.

Each docking experiment was derived from 100 different runs that were set to terminate after a maximum of 250,000 energy evaluations or 27,000 generations, yielding 100 docked conformations Docking protocol was set for 100 different runs with a maximum of 25×10$^5$ energy evaluations and 27,000 repetitions. Other docking parameters were defaulted. Docked poses were selected with reference to the criteria of scoring functions and protein-ligand interaction. Discovery Studio 2017 R2 was used to visualize the protein-ligand interaction and generate interaction values.

Example 1: Purification of Novel Compound

A hot-water extract of bracken fern was fractionated with ethyl acetate and butanol to yield seven fractions. Each fraction was subjected to HPLC to isolate pterosin compounds and the novel compound.

In brief, 200-250 g of bracken ferns collected from an area of Gapyeong-gun, Gyenggi-do, South Korea was cleansed and steamed for 24 hours with 1.5 L of water in a steaming vessel (OSK-2002, Hongsambaksa, Well Sosana™, Dae-Woong Pharmaceutical Co. Ltd.), after which 3.5 L of water was further added and then the bracken ferns were aged for 72 hours. The hydrothermal extract thus obtained was stored in a refrigeration manner until use. The hydrothermal extract was added and well mixed with an equal volume of ethyl acetate (EA) and the EA layer thus formed was dried using a rotary evaporator. The resulting EA extract was dissolved in a minimum amount of DMSO and then diluted in water. In this regard, the dilution was made up to 70% of the original volume of the hydrothermal extract, with the expectation of a yield of approximately 70%.

The EA extract was divided into seven fractions by silica gel column chromatography using chloroform ($CHCl_3$) and methanol. Then, each fraction was analyzed by Prep-HPLC. Fractions 2, 4, 5, 6, and 7 were analyzed to contain the novel compound [Compound 2, comp.1] and pterosin and derivatives thereof, as listed in Table 1, below. The extraction procedure is as illustrated in FIG. 1.

Separately, the aqueous layer remaining upon treatment with EA was added and well mixed with an equal volume of butanol. The butanol layer thus formed was dried using a rotary evaporator. The resulting butanol extract (Bu extract) was dissolved in a minimum amount of DMSO and then diluted in water. In this regard, the dilution was made up to 70% of the original volume of the hydrothermal extract, with the expectation of a yield of approximately 70%.

The Bu extract was divided into nine fractions by silica gel column chromatography using chloroform ($CHCl_3$) and methanol. Then, each fraction was analyzed by Prep-HPLC. Fraction 6 was analyzed to contain pterosin derivatives, as listed in Table 1, below. The extraction procedure is as illustrated in FIG. 1.

HPLC conditions for extracting single compounds from EA-2 fraction and Bu-6 fraction are given in FIG. 2.

TABLE 1

| Compound # (FIG. 1 comp.) | Structural Formula | Name |
|---|---|---|
| 2 (comp. 1) | 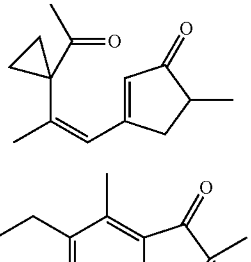 | 3-[2-(1-Acetylcyclopropyl)-1-propenyl)-5-methyl-2-cyclopenten-1-one |
| 3 (comp. 2) | 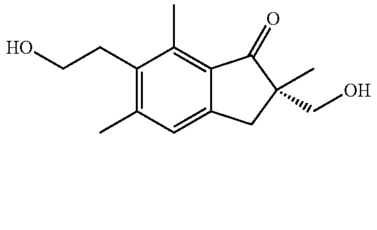 [SMILES: Cc1cc2c(c(C)c1CCO)C(=O)[C@](C)(CO)C2] | (2S)-pterosin A |

TABLE 1-continued
| Compound # (FIG. 1 comp.) | Structural Formula | Name |
| --- | --- | --- |
| 4 (comp. 3) | 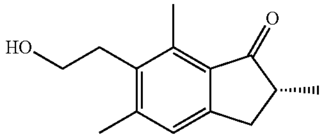 [SMILES: Cc1cc2c(c(C)c1CCO)C(=O)[C@H](C)C2] | (2R)-pterosin B |
| 5 | 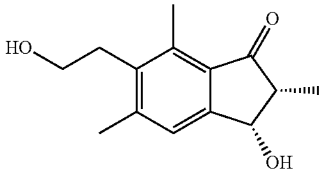 [SMILES: Cc1cc2c(c(C)c1CCO)C(=O)[C@H](C)[C@@H]2O] | (2R,3S)-pterosin C |
| 6 | 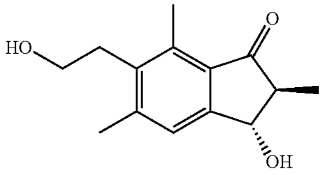 [SMILES: Cc1cc2c(c(C)c1CCO)C(=O)[C@@H](C)[C@@H]2O] | (2S,3S)-pterosin C |
| 7 (comp. 5) | 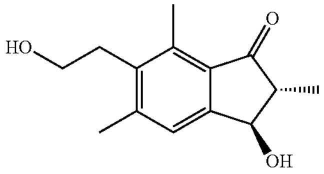 [SMILES: Cc1cc2c(c(C)c1CCO)C(=O)[C@H](C)[C@H]2O] | (2R,3R)-pterosin C |
| 8 (comp. 4) | 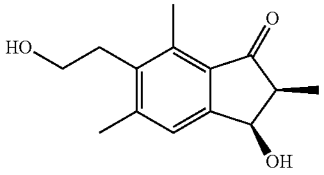 [SMILES: Cc1cc2c(c(C)c1CCO)C(=O)[C@@H](C)[C@H]2O] | (2S,3R)-pterosin C |
| 9 (comp. 6) | 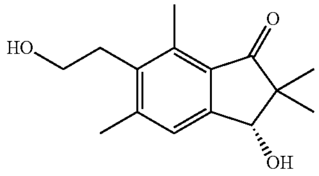 [SMILES: Cc1cc2c(c(C)c1CCO)C(=O)C(C)(C)[C@@H]2O] | (3R)-Pterosin D |
| 10 (comp. 7) | 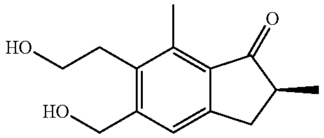 [SMILES: Cc1c(CCO)c(CO)cc2c1C(=O)[C@@H](C)C2] | (2S)-pterosin P |
| 11 (comp. 8) | 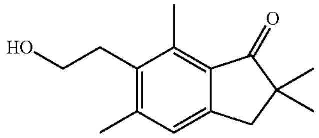 [SMILES: Cc1cc2c(c(C)c1CCO)C(=O)C(C)(C)C2] | pterosin Z |

TABLE 1-continued
| Compound # (FIG. 1 comp.) | Structural Formula | Name |
| --- | --- | --- |
| 12 (comp. 9) | 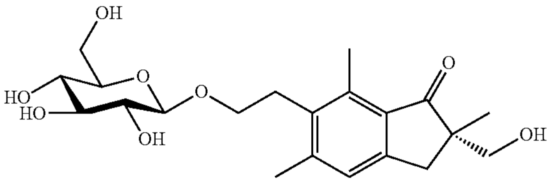 | (2S)-pteroside A |
| 13 (comp. 10) | 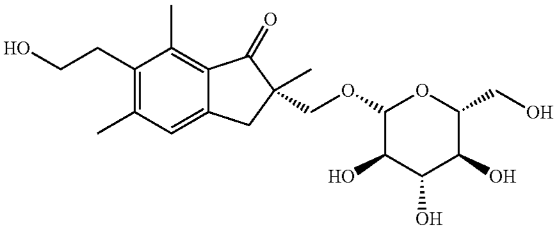 | (2S)-pteroside $A_2$ |
| 14 (comp. 11) | 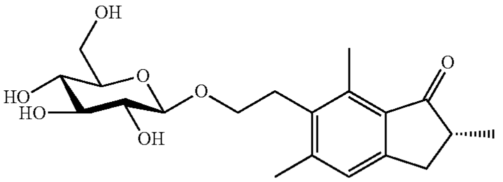 | (2R)-pteroside B |
| 15 (comp. 12) | 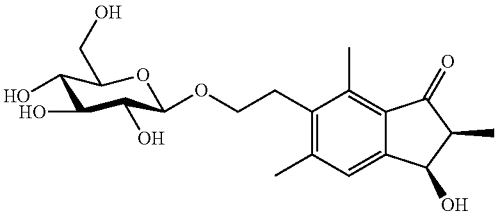 | (2S,3R)-pteroside C |
| 16 (comp. 13) | 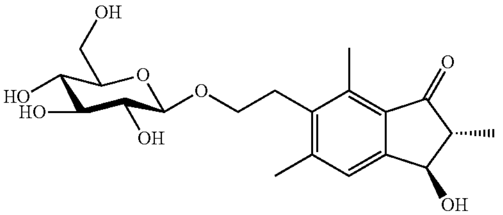 | (2R,3R)-pteroside C |
| 17 (comp. 14) | 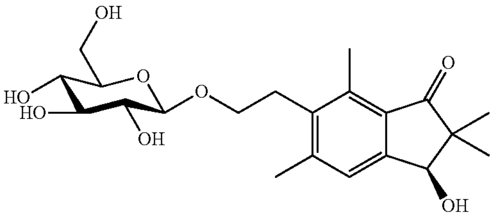 | (3S)-pteroside D |
| 18 (comp. 15) | 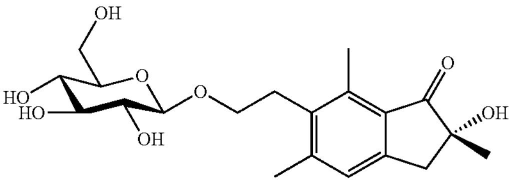 | (−)-pteroside N |

TABLE 1-continued
| Compound # (FIG. 1 comp.) | Structural Formula | Name |
| --- | --- | --- |
| 19 (comp. 16) | 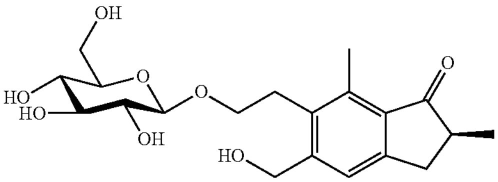 | (2S)-pteroside P |
| 20 (comp. 17) | 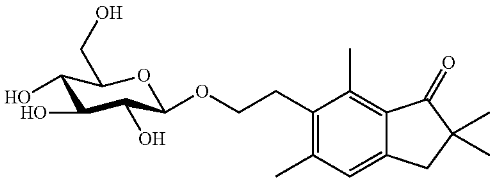 | pteroside Z |
| 21 | 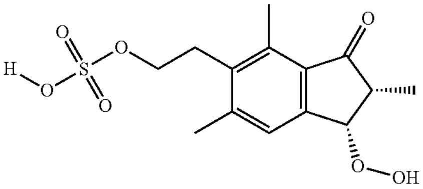 [SMILES: Cc1cc2c(c(C)c1CCOS(=O)(=O)O)C(=O)[C@H](C)[C@@H]2OO] | (2R,3S)-sulfated pterosin C |
| 22 | 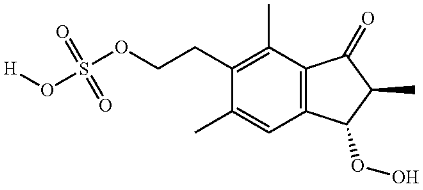 [SMILES: Cc1cc2c(c(C)c1CCOS(=O)(=O)O)C(=O)[C@@H](C)[C@@H]2OO] | (2S,3S)-sulfated pterosin C |
| 23 | 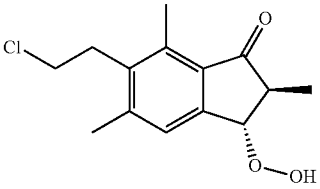 [SMILES: Cc1cc2c(c(C)c1CCCl)C(=O)[C@@H](C)[C@@H]2OO] | pterosin J |
| 24 | 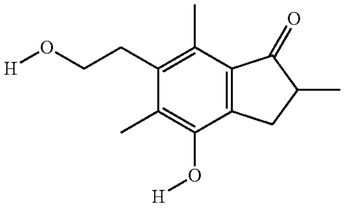 [SMILES: Cc1c(O)c2c(c(C)c1CCO)C(=O)C(C)C2] | pterosin M |
| 25 | 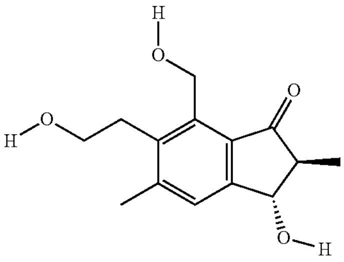 [SMILES: Cc1cc2c(c(CO)c1CCO)C(=O)[C@@H](C)[C@@H]2O] | pterosin S |

Example 2: Identification of Novel Compound and Derivatives Thereof

The structure of the novel compound isolated and purified in Example 1 was identified by nuclear magnetic resonance (NMR) and mass spectroscopy (MS).

On the basis of the NMR data shown in FIG. 3, the isolated and purified compound was identified to be 3-[2-(1-acetylcyclopropyl)-1-propenyl]-5-methyl-2-cyclopenten-1-one (3-[2-(1-acetylcycloproply)-1-propenyl]-5-methyl-2-cyclopenten-1-one), which corresponds to compound 2 in Table 1. It was found to be a novel compound that is first isolated from nature and has not yet been reported thus far.

Example 3: Assay for Cytotoxicity of Compounds (MTT Assay)

In order to examine whether the compounds of the present disclosure have toxicity to cells, the following experiment was conducted.

The normal cell line NIH3T3 (mouse embryo fibroblast cell-line) and the cancerous cell line B16F10 (mouse melanoma cell-line) were separately grown in 96-well plates and incubated for 48 hours with predetermined concentrations of each of the compounds. After additional incubation with MTT, absorbance at 550 nm was read using a microplate reader. Absorbance is an index accounting for a number of viable cells and was used to calculate cell proliferation rates according to the following formula. All experiments were conducted three times for reproducibility.

$$\text{Cell proliferation rate (\%)}=OD_{550}(\text{sample})/OD_{550}(\text{control})$$

Then, $LD_{50}$ (Lethal Dose 50) values were calculated on the basis of changes in the cell proliferation rate.

The results are given in Table 2. As shown, the $LD_{50}$ of pterosin A for the cancerous cells was 522±25 μM, which was the lowest among those detected in the compounds. $LD_{50}$ values were measured to be 3,110±130 μM for pterosin B and 553±37 μM for pterosin Z in the normal cells and 618±71 μM for pterosin Z in the cancerous cells. Except for them, the other compounds were measured to have $LD_{50}$ values higher than 5000 μM in both the normal and the cancerous cells.

These results indicate that pterosin Z (Compound 11) is slightly toxic to cells and pterosin A (Compound 3) has slight cytotoxicity against cancerous cells only, while the other compounds are toxic to none of the normal and the cancerous cells.

In addition, the novel compound (Compound 2) was measured to have $LD_{50}$ values of 1,550 μM and 688 μM against the normal cells and the cancerous cells, respectively. Thus, the novel compound is identified to be almost non-toxic to normal cells and slightly toxic to cancerous cells.

TABLE 2

| | $LD_{50}$ (μM) | |
|---|---|---|
| Compounds | Normal cell NIH3T3 | Cancer cell 816F10 |
| 3-[2-(1-acetylcycloproply)-1-propenyl]-5-methyl-2-cyclopenten-1-one | 1,550 ± 100 | 688 ± 17 |
| (2S)-Pterosin A | >5,000 | 522 ± 25 |
| (2,R)-Pterosin B | 3,110 ± 130 | >5,000 |
| (2R,3S)-Pterosin C | >5,000 | >5,000 |
| (2S,3S)-Pterosin C | >5,000 | >5,000 |

TABLE 2-continued

| | $LD_{50}$ (μM) | |
|---|---|---|
| Compounds | Normal cell NIH3T3 | Cancer cell 816F10 |
| (2R,3R)-pterosin C | >5,000 | >5,000 |
| (2S,3R)-pterosin C | >5,000 | >5,000 |
| (3R)-Pterosin D | >5,000 | >5,000 |
| (2S)-Pterosin P | >5,000 | >5,000 |
| PterosinZ | 553 ± 37 | 618 ± 71 |
| (2S)-Pteroside A | >5,000 | >5,000 |
| (2S)-Pteroside A, | >5,000 | >5,000 |
| (2R) Pteroside B | >5,000 | >5,000 |
| (2S,3R)-Pteroside C | >5,000 | >5,000 |
| (2R,3R)-Pteroside C | >5,000 | >5,000 |
| (3S)-Pteroside D | >5,000 | >5,000 |
| (—)-Pteroside N | >5,000 | >5,000 |
| (2S)-Pteroside P | >5,000 | >5,000 |
| Pteroside Z | >5,000 | >5,000 |

Example 4: Inhibitory Effect of Inventive Compounds on BACE1

BACE1 is an enzyme promotive of the production of β-amyloid, which destroys neurons. In order to examine the effects on the compounds of Table 1 on the activity of BACE1, IC(inhibition concentrations)$_{50}$ values were determined by measuring BACE1 activity in vitro according to Experimental Methods. Each compound was dissolved in 10% DMSO and applied at various concentrations up to 125 μM.

The results are given in Table 3, below. As shown, Compounds 2, 6, 7, 8, 16, and 17 have $IC_{50}$ values lower than or similar to that of quercetin.

Of them, the positive control quercetin and Compound 2 (novel compound), Compound 4 ((2R)-Pterosin B), Compound 7 ((2R, 3R)-Pterosin C), Compound 8 ((2S, 3R)-Pterosin C), Compound 14 ((2R)-Pteroside B), Compound 16 ((2R, 3R)-Pteroside C), and Compound 17 ((3S)-Pteroside D), which have low $IC_{50}$ values, were examined for inhibiting mechanisms against BACE 1 enzyme activity and for Ki through enzyme kinetics experiments using Dixon plot and Lineweaver plot.

The results are given in Table 4 (enzymatic kinetics of the compounds of the present disclosure based on Dixon plot and Lineweaver plot). As shown, the BACE1 inhibition mechanism was identified to be of noncompetitive type for Compounds 4, 8, and 14 and of mixed type for Compounds 7, 16, and 17. Having very low Ki values, all of Compound 4, 7, 8, 14, 16, and 17 were observed to bind strongly to BACE1 and thus they are very potent inhibitors against BACE1.

Figure 7:
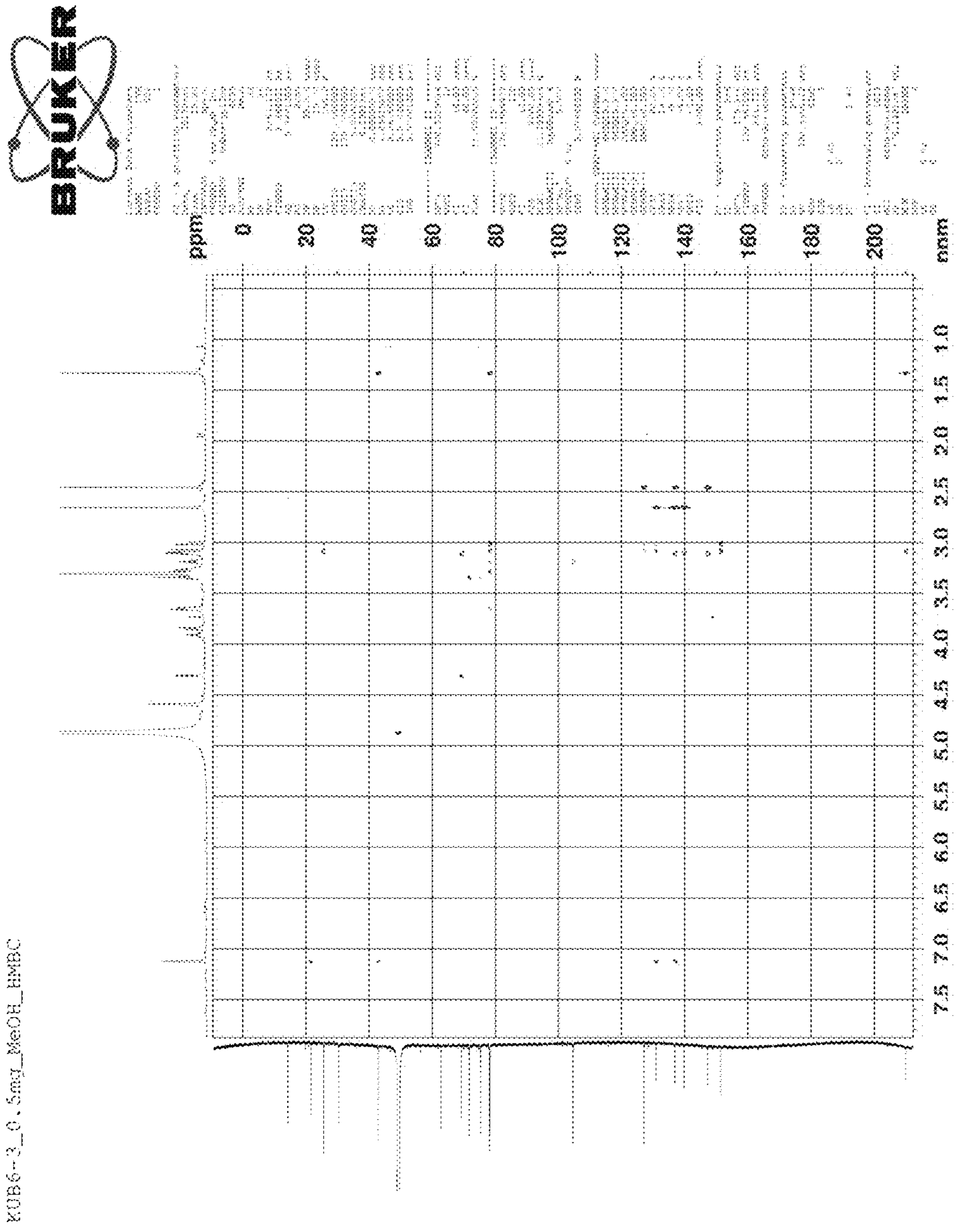
FIG. 7 shows HMBC analysis results for pteroside N (Compound 18, comp.15).
Figure 8:
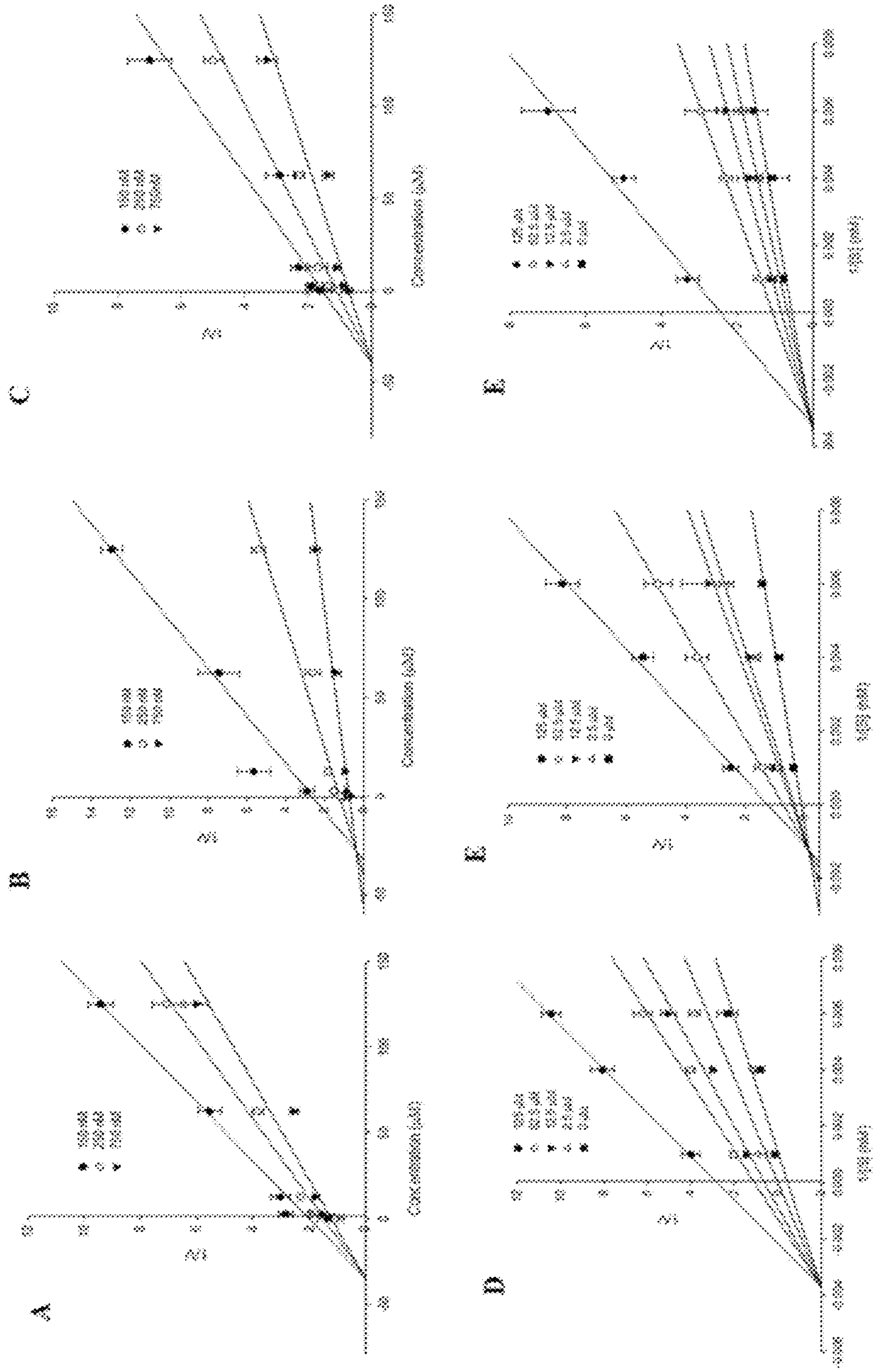
FIG. 8 shows BACE1 activity inhibition mechanisms and Ki values of (2S, 3R)-pterosin C cis-isomer (A, D), (2R, 3R)-pterosin C trans-isomer (B, E), and pterosin B (C, F) as evaluated by Dixon plots (X-axis: concentration of the novel compound, Y-axis: 1/initial reaction rate of enzyme) (a) and Lineweaver plots (X-axis: 1/substrate concentration, Y-axis: /initial reaction rate of enzyme), wherein graphs A to C represent Dixon plots and graphs D to F represent Lineweaver plots.

In addition, an enzyme kinetics experiment was conducted using the Lineweaver plot and Dixon plot (see FIG. 7) in order to examine the BACE1 inhibition mechanism of the novel compound (Compound 2). As shown in Table 3, the novel compound has a Ki value of as low as 19.0 μM, which explains strong binding force to BACE1. The inhibition mechanism was found to be of mixed type. The results of the experiment indicate that the novel compound of the present disclosure is a very potent inhibitor against BACE1.

Consequently, the compounds extracted according to the method of the present disclosure have excellent inhibitor activity against BACE1, which is an enzyme producing β-amyloid causative of degenerative brain disease.

TABLE 3

| Compounds | $IC_{50}$ (μM) BACE1 |
|---|---|
| 3-[2-(1-acetylcycloproply)-1-propenyl]-5-methyl-2-cyclopenten-1-one | 19.4 ± 1.7 |
| (2S)-Pterosin A | 64.9 ± 5.1 |
| (2R)-Pterosin B | 18.0 ± 2.0 |
| (2S,3R)-Pterosin C | 14.1 ± 1.6 |
| (2R,3R)-Pterosin C | 15.9 ± 3.5 |
| (3R)-Pterosin D | 56.3 ± 3.9 |
| (2S)-Pterosin P | 40.8 ± 4.1 |
| Pterosin Z | 48.7 ± 3.2 |
| (2S)-Pteroside A | 84.6 ± 6.0 |
| (2S)-Pteroside $A_2$ | 94.4 ± 4.5 |
| (2R)-Pteroside B | 43.4 ± 3.0 |
| (2S,3R)-Pteroside C | 28.9 ± 2.2 |
| (2R,3R)-Pteroside C | 9.74 ± 1.9 |
| (3S)-Pteroside D | 10.7 ± 1.5 |
| (−)-Pteroside N | 30.6 ± 1.8 |
| (2S)-Pteroside P | 81.3 ± 3.9 |
| Pteroside Z | 60.0 ± 4.3 |
| Quercetin[a] | 18.8 ± 1.0 |

Quercetin[a]: positive control for BACE1.

TABLE 4

| Compounds | Ki and inhibition type | | | | | |
|---|---|---|---|---|---|---|
| | BACE1 | | Acetylcholinesterase | | Butyrylcholinesterase | |
| | Ki (μM) | Inhibition type | Ki (μM) | Inhibition type | Ki (μM) | Inhibition type |
| 3-[2-(1-acetylcycloproply)-1-propenyl]-5-methyl-2-cyclopenten-1-one | 19.0 | Mixed-type | | | | |
| (2R)-Pterosin B | 38.3 | Noncompetitive | 12.1 | Mixed-type | 53.5 | Noncompetitive |
| (2S,3R)-Pterosin C | 33.8 | Noncompetitive | 16.3 | Mixed-type | 29.9 | Noncompetitive |
| (2R,3R)-Pterosin C | 27.6 | Mixed-type | 29.6 | Noncompetitive | 4.77 | Mixed-type |
| (2R)-Pteroside B | 72.5 | Noncompetitive | 4.89 | Mixed-type | 22.6 | Mixed-type |
| (2R,3R)-Pteroside C | 12.6 | Mixed-type | | | | |
| (3S)-Pteroside D | 16.5 | Mixed-type | | | | |

Example 5: Inhibitory Effect of Pterosin Compounds on Cholinesterases

The compounds of Table 1 were evaluated for anti-Alzheimer activity. In this regard, inhibitory activity against AChE (acetylcholinesterase) and BChE (butyrylcholinesterase), which lyse acetylcholine in the central nervous system, was measured according to the Experimental Method to calculate IC(inhibition concentrations)$_{50}$ values. Each compound was dissolved in 10% DMSO and applied at various concentrations up to 125 μM.

Cholinesterase is an enzyme that catalyzes the hydrolysis of acethylcholine, which is a neurotransmitter serving to improve thought and memory. Acetylcholine hydrolysis activity is much more potent in AChE than BChE.

Figure 5:
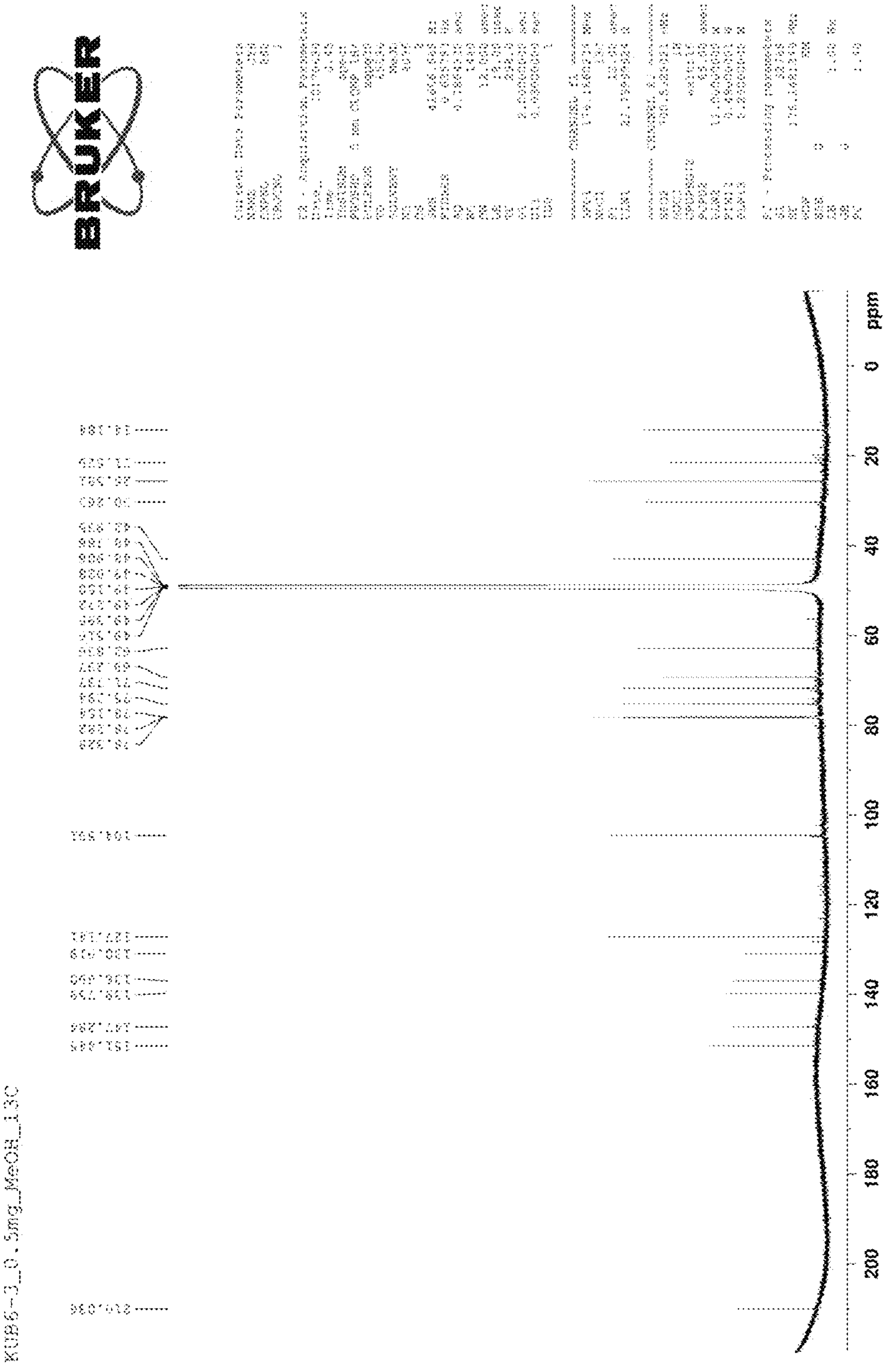
FIG. 5 shows a $^{13}$C-NMR spectrum for pteroside N (Compound 18, comp.15).
Figure 6:
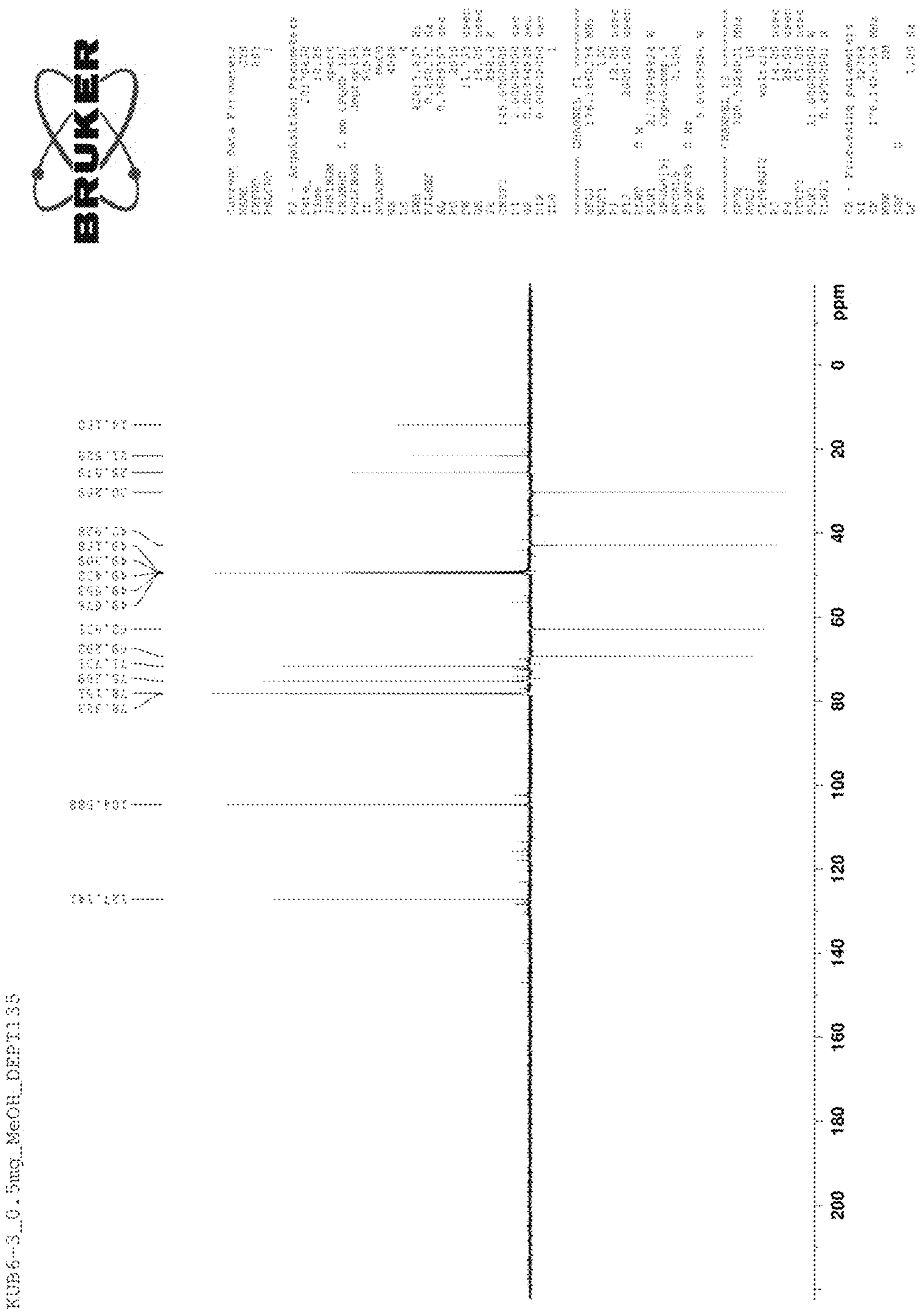
FIG. 6 shows a DEPT 1 spectrum for pteroside N (Compound 18, comp.15).

As shown in FIG. 5, each of the compounds was measured to have an $IC_{50}$ value higher than that of the positive control berberine. In the compounds, the $IC_{50}$ value against AChE was measured to be the lowest for Compound 14 and the highest for Compound 2. In addition, the $IC_{50}$ value against BChE was measured to be the lowest for Compound 16 and the highest for Compound 9.

Among the pterosin compounds extracted by the method of the present disclosure, Compound 14 (pteroside B), Compound 16 (pteroside C), and Compound 4 (Pterosin B) were found to have excellent AChE inhibition activity as proven by the results. In addition, Compound 6 (pterosin C trans-isomer), Compound 14 (pteroside B), and Compound 20 (pteroside Z) showed excellent BChE inhibition activity.

Figure 9:
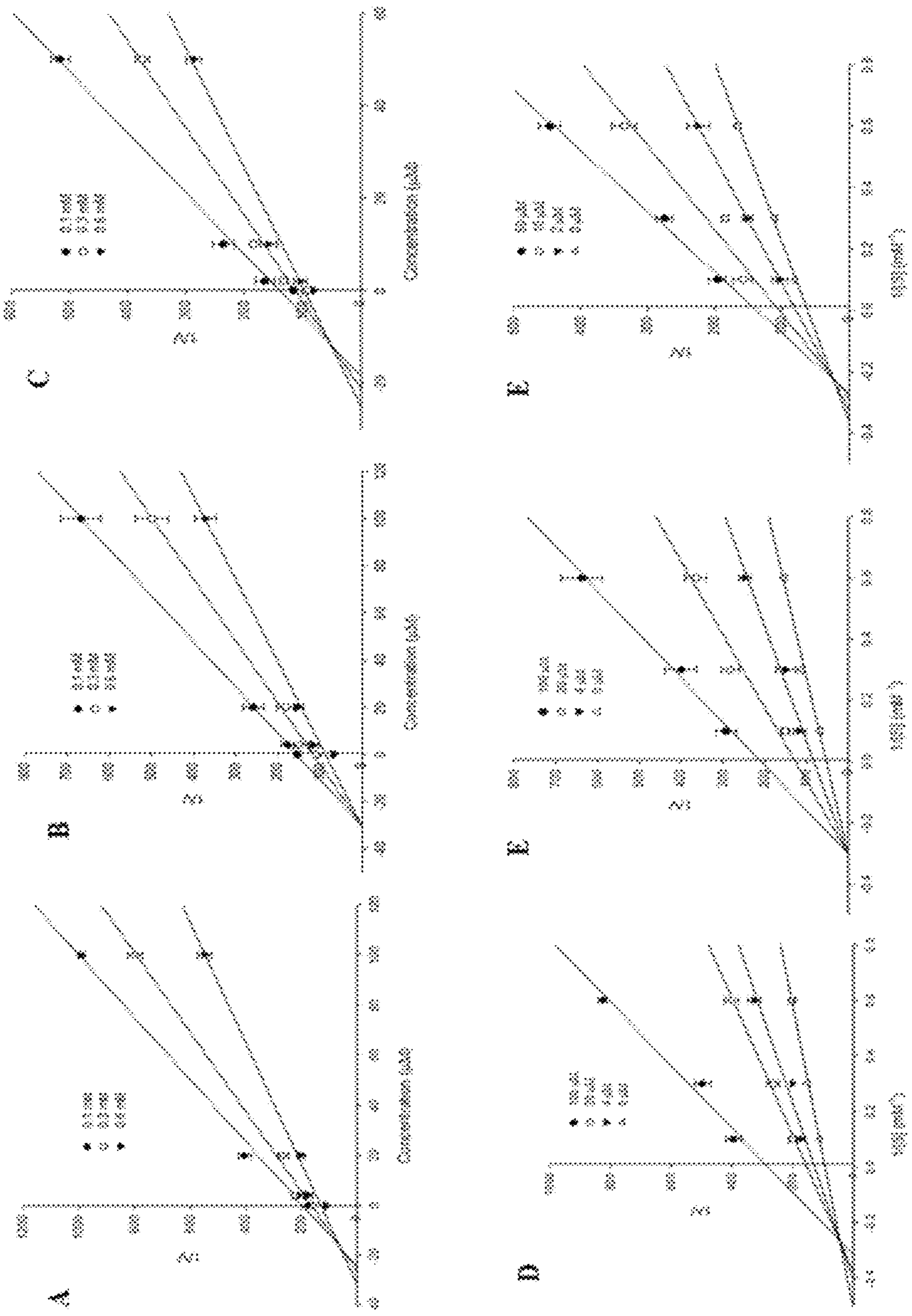
FIG. 9 shows AChE activity inhibition mechanisms and Ki values of (2S, 3R)-pterosin C cis-isomer (A, D), (2R, 3R)-pterosin C trans-isomer (B, E), and pterosin B (C, F) as evaluated by Dixon plots (X-axis: concentration of the novel compound, Y-axis: 1/initial reaction rate of enzyme) (A, B, C) and Lineweaver plots (X-axis: 1/substrate concentration, Y-axis: 1/initial reaction rate of enzyme) (D, E, F).
Figure 10:
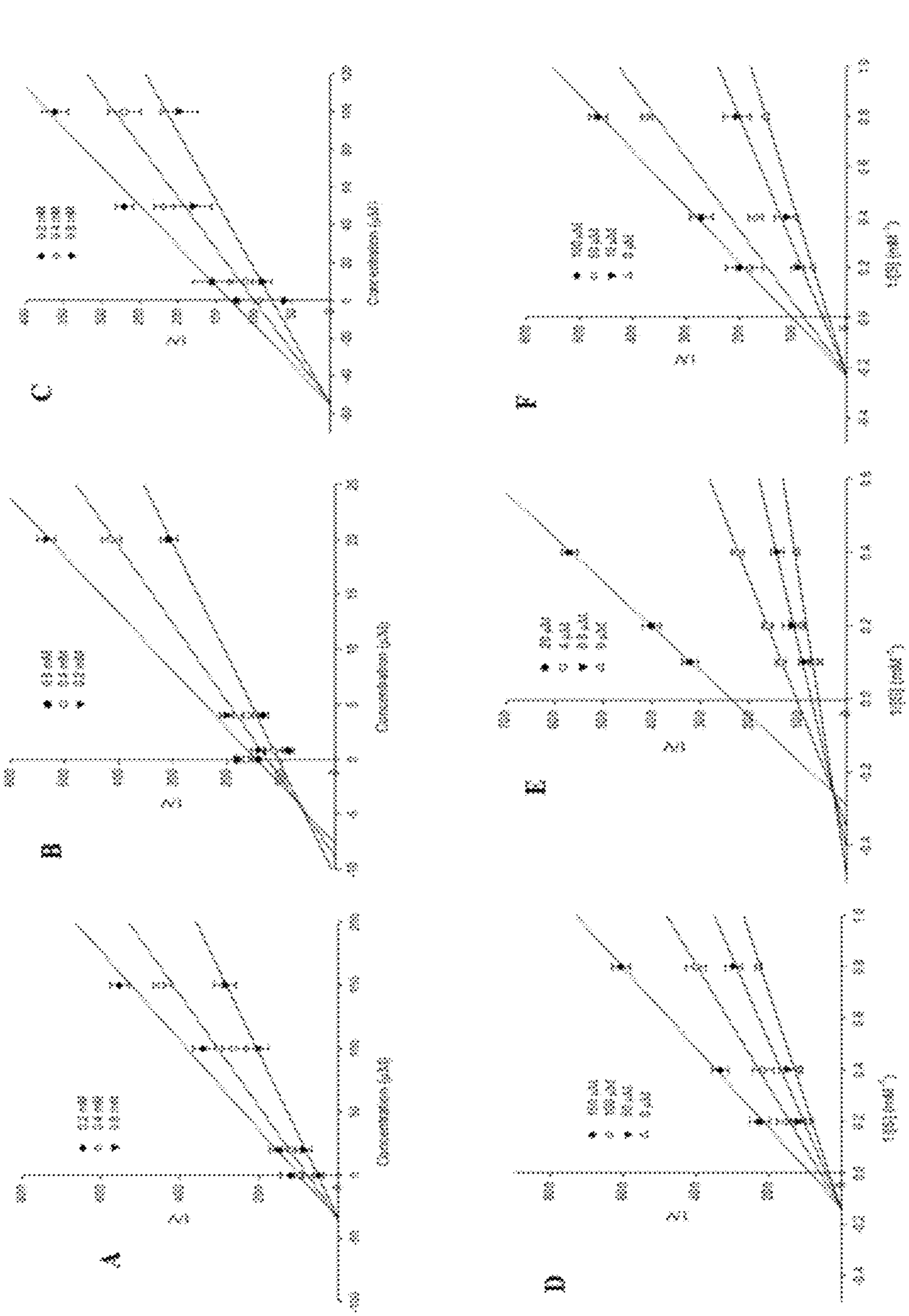
FIG. 10 shows BChE activity inhibition mechanisms and Ki values of (2S, 3R)-pterosin C cis-isomer (A, D), (2R, 3R)-pterosin C trans-isomer (B, E), and pterosin B (C, F) as evaluated by Dixon plots (X-axis: concentration of the novel compound, Y-axis: 1/initial reaction rate of enzyme) (A, B, C) and Lineweaver plots (X-axis: 1/substrate concentration, Y-axis: 1/initial reaction rate of enzyme) (D, E, F).

Of them, the positive control berberine and Compound 2 (novel compound), Compound 4 ((2R)-Pterosin B), Compound 7 ((2R, 3R)-Pterosin C), Compound 8 ((2S, 3R)-Pterosin C), and Compound 14 ((2R)-Pteroside B), which have low $IC_{50}$ values, were examined for inhibiting mechanisms against AChE and BChE enzyme activity nd for Ki through enzyme kinetics experiments using Dixon plot and Lineweaver plot (see FIGS. 9 and 10).

The results are given in Table 4. As shown, the AChE inhibition mechanism was identified to be of mixed type for Compounds 4, 8, and 14 and of noncompetitive type for Compound 7 while the BChE inhibition mechanism was identified to be of noncompetitive type for Compounds 4 and 8 and of mixed type for Compounds 7 and 14. Having very low Ki values, all of Compounds 4, 7, 8, and 14 were observed to bind strongly to both AChE and BChE and thus they are very potent inhibitors against AChE and BChE.

Consequently, the pterosin compounds extracted according to the method of the present disclosure were found to have the ability to maintain certain levels of acetylcholine, which is a neurotransmitter responsible for the cognitive functions of the brain, such as thinking, memory, etc., by inhibiting the activities of AChE and BChE, which are enzymes lysing acetylcholine.

TABLE 5

| Compounds | $IC_{50}$ (μM) Acetylcholine Esterase Mean ± SEM | $IC_{50}$ (μM) Butyrylcholine esterase Mean ± SEM | SI[b] |
|---|---|---|---|
| 3-[2-(1-acetylcycloproply)-1-propenyl]-5-methyl-2-cyclopenten-1-one | 87.7 ± 1.6 | 72.9 ± 0.73 | 0.83 |
| (2S)-Pterosin A | 56.7 ± 2.6 | 67.3 ± 3.3 | 1.2 |
| (2R)-Pterosin B | 16.2 ± 1.0 | 48.1 ± 0.59 | 3.0 |
| (2S,3R)-Pterosin C | 12.8 ± 0.79 | 44.3 ± 1.0 | 3.5 |
| (2R,3R)-Pterosin C | 23.2 ± 4.6 | 20.3 ± 0.88 | 0.89 |
| (3R)-Pterosin D | 68.7 ± 3.7 | >125 | |
| (2S)-Pterosin P | 17.8 ± 0.62 | 55.9 ± 5.6 | 3.1 |
| Pterosin Z | 46.5 ± 3.4 | 80.1 ± 6.8 | 1.7 |
| (2S)-Pteroside A | 110 ± 3.0 | 19.4 ± 0.22 | 0.17 |
| (2S)-Pteroside $A_2$ | 39.3 ± 1.9 | 119 ± 2.5 | 3.0 |
| (2R)-Pteroside B | 2.55 ± 0.23 | 17.6 ± 3.1 | 6.9 |
| (2S,3R)-Pteroside C | 9.17 ± 0.82 | 13.0 ± 0.14 | 1.4 |
| (2R,3R)-Pteroside C | 3.77 ± 0.38 | 5.29 ± 0.82 | 1.4 |
| (3S)-Pteroside D | 27.4 ± 1.2 | 19.3 ± 0.17 | 0.70 |
| (−)-Pteroside N | 4.47 ± 0.29 | 7.39 ± 0.99 | 1.7 |
| (2S)-Pteroside P | 57.5 ± 3.2 | 33.2 ± 3.0 | 0.57 |

TABLE 5-continued

| Compounds | IC50 (μM) Acetylcholine Esterase Mean ± SEM | Butyrylcholine esterase Mean ± SEM | SI[b] |
|---|---|---|---|
| Pteroside Z | 22.4 ± 2.2 | 5.31 ± 0.19 | 0.24 |
| Berberine[a] | 0.39 ± 0.01 | 3.31 ± 0.12 | 8.5 |

Berberine[a]: positive control for cholinesterases (AChE and BChE).

SI[b]: selectivity index (BChE/AChE) indicating which of AChE and BChE is more specifically inhibited.

Example 6: Docking Results of Compounds to Active Sites of BACE1, AChE, and BChE BACE1, AChE, and BChE have several crystalline structures. Of them, human PDB was selected in consideration of wild-type structures, co-crystallized ligands, and solvents of structures. Selection was made of X-ray crystal structures of BACE1 forming a complex with QUAD (PDB code: 2WJO); AChE forming a complex with E2020 (PDB code: 4EY7); and BChE forming a complex with 3F9 (PDB code: 4TPK).

The compounds given in Table 1 were investigated for binding patterns. Docking studies were conducted for compounds selected for examination of structure activity correlation. (2R, 3R)-Pteroside C was found to be a potent inhibitor against BACE1, AChE, and BChE as measured by the enzyme inhibition assay. Therefore, (2R, 3R)-pteroside C was selected as a representative compound for docking. In addition, quercetin and berberine, which were used as positive controls in the enzyme inhibition assay, were subjected to the docking simulation.

The molecular docking simulation results are summarized in FIG. 12. As shown, (2R, 3R)-pteroside C strongly interacts with the active site of BACE1, with the bonding energy detected at −6.77 kcal/mol which is lower than the quercetin bonding energy −5.68 kcal/mol.

In addition, the bonding energy of the compound was −6.85 kcal/mol for AChE, which is higher than the berberine bonding energy −8.61 kcal/mol, and −5.99 kcal/mol for BChE, which is slightly higher than the berberine bonding energy −6.67 kcal/mol.

These results show high affinities and strong binding potentials the compounds of the present disclosure for the active sites of BACE1, AChE, and BChE, indicating that the compounds bind to the enzymes and inhibit the enzymatic activities.

Figure 13A:
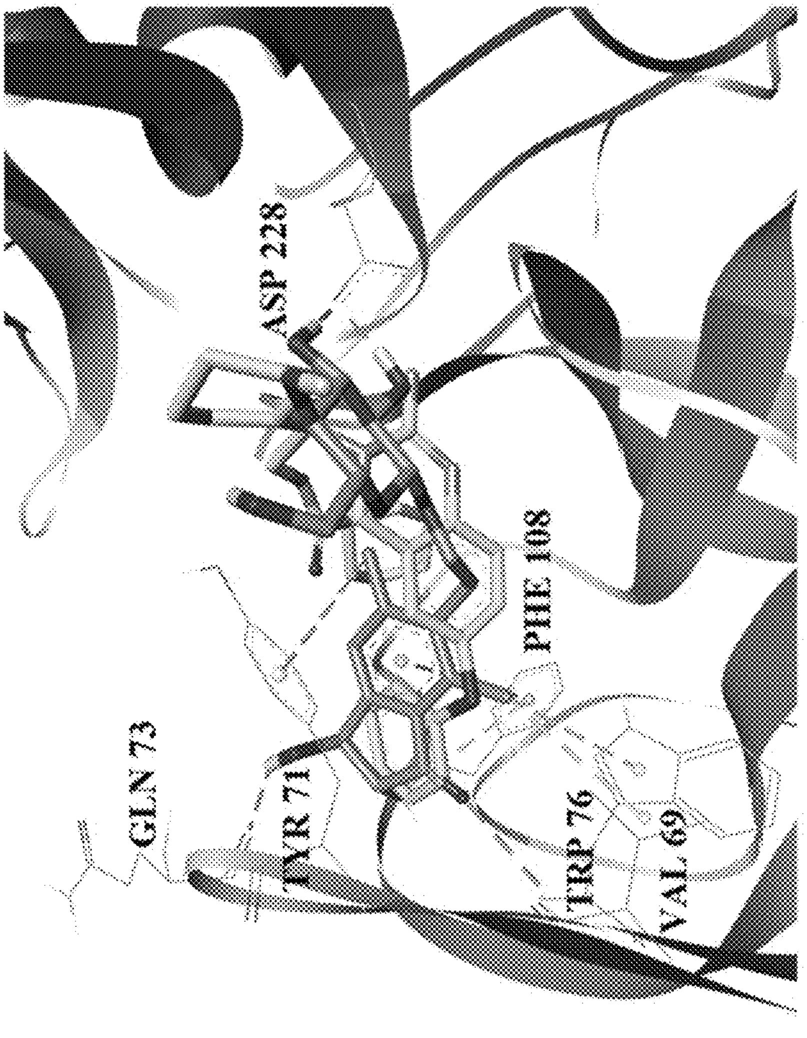
FIG. 13 illustrates the interaction of (2R, 3R)-pteroside C (Compound 16) with human BACE1 to inhibit the activity of BACE1 in a 3D image (13*a*) and a plane image (13*b*), wherein the green color accounts for a hydrogen bond, the pink for hydrophobic interaction, and the purple color for a n-sigma bond.
Figure 13B:
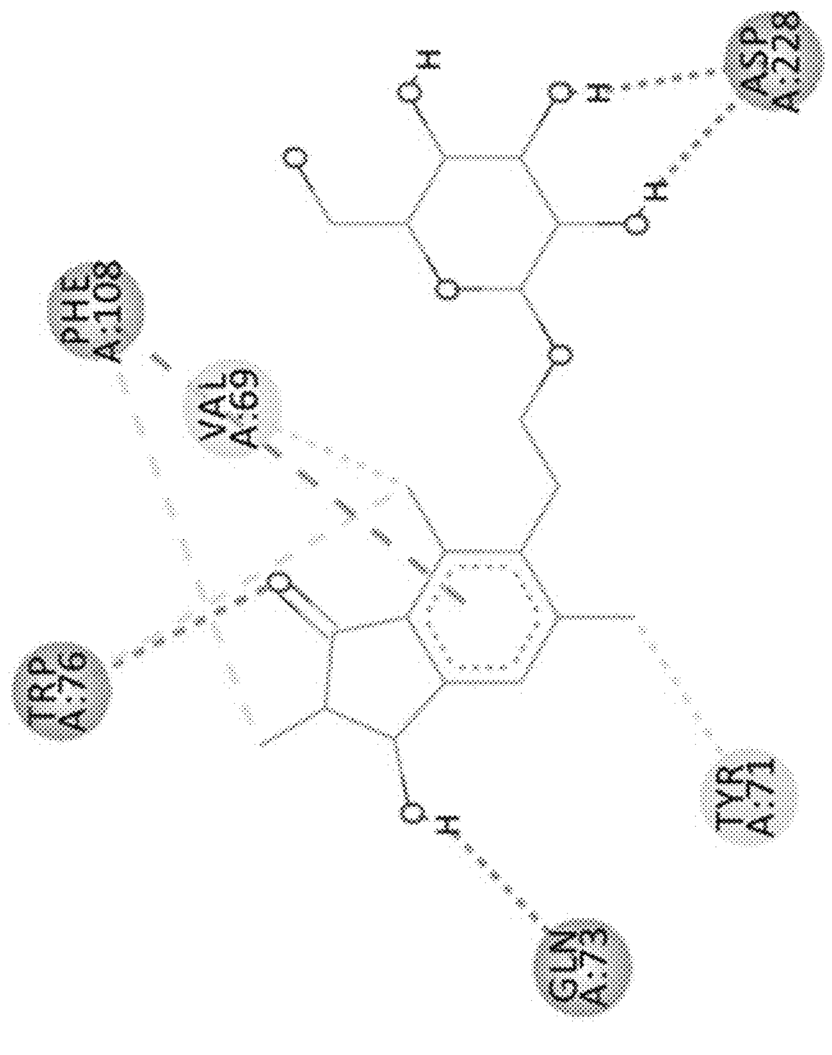
Figure 14A:
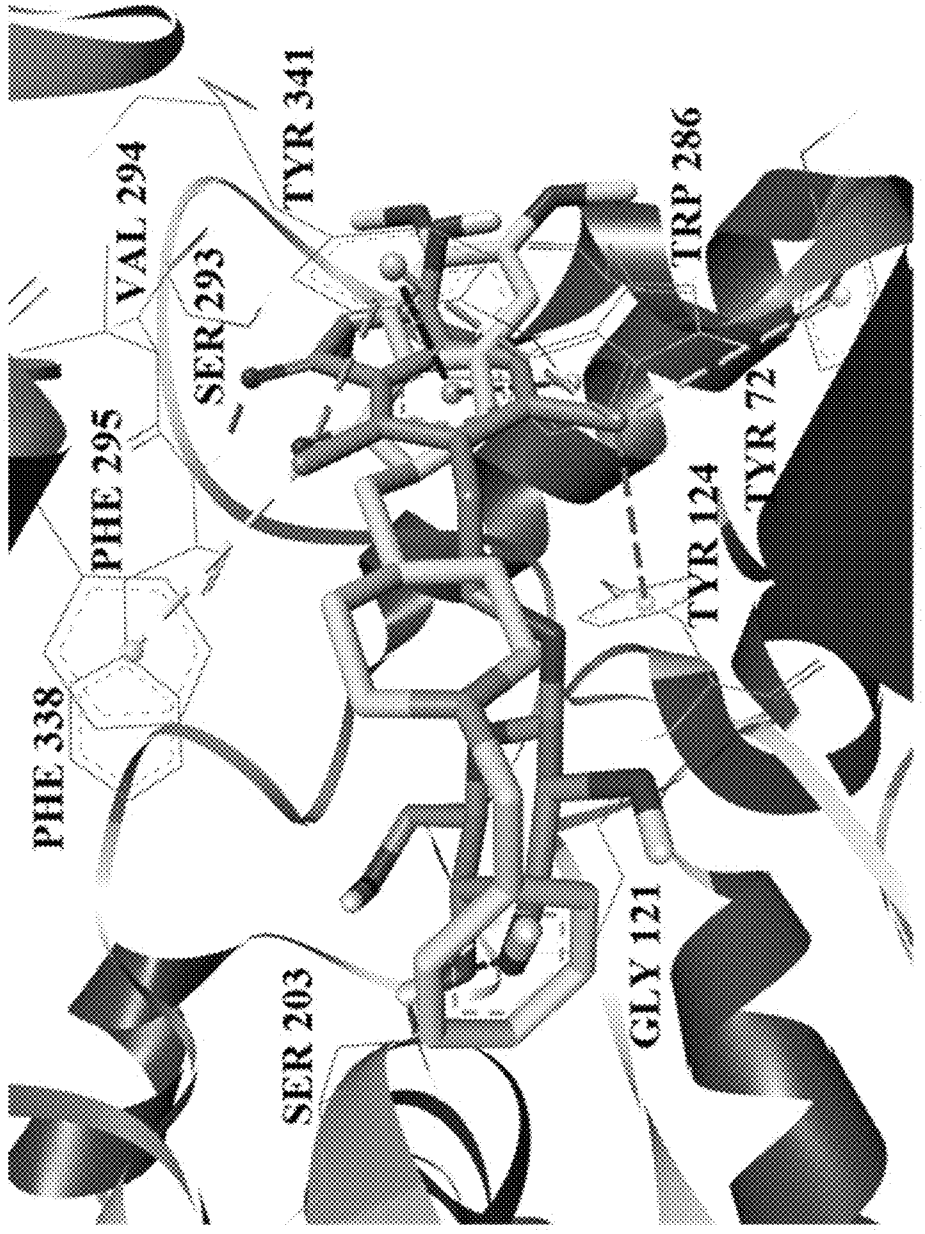
FIG. 14 illustrates the interaction of (2R, 3R)-pteroside C (Compound 16) with human AChE to inhibit the activity of AChE in a 3D image (14*a*) and a plane image (14*b*), wherein the green color accounts for a hydrogen bond, the pink for hydrophobic interaction, and the purple color for a n-sigma bond.
Figure 14B:
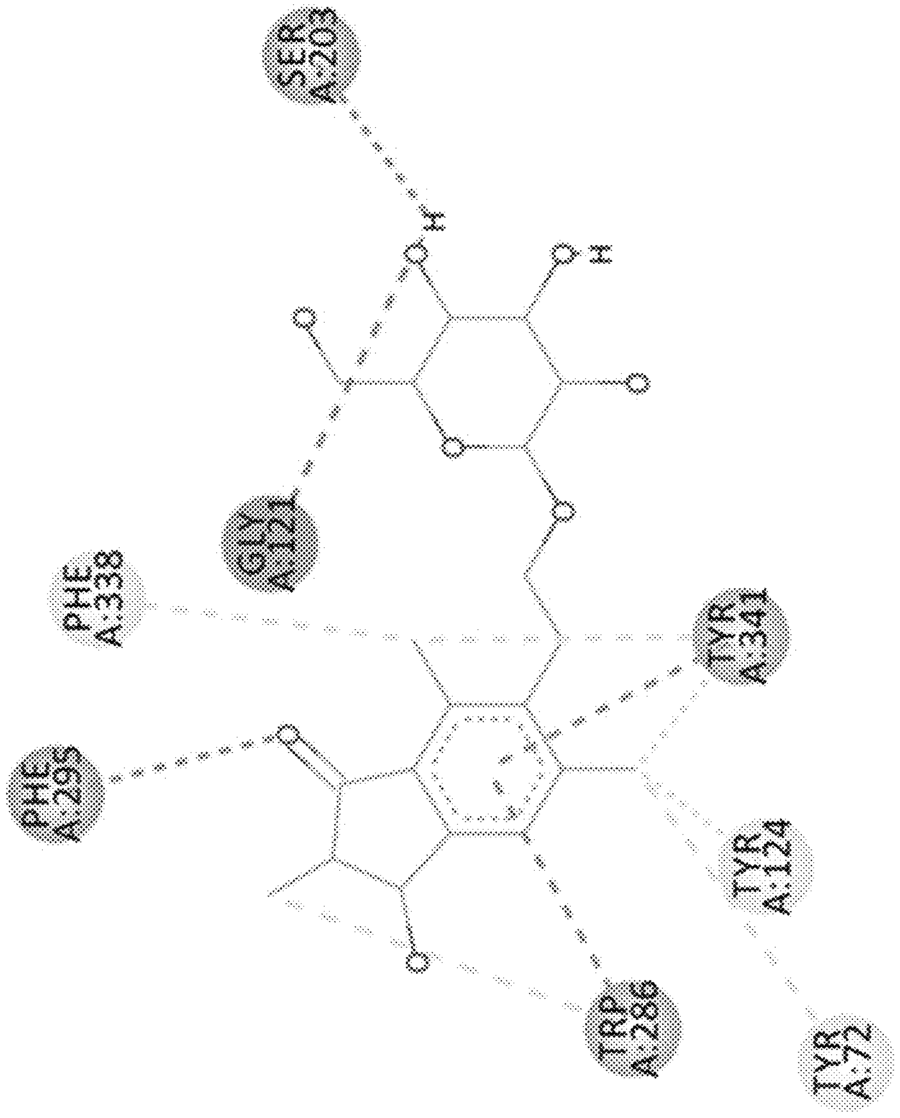
Figure 15A:
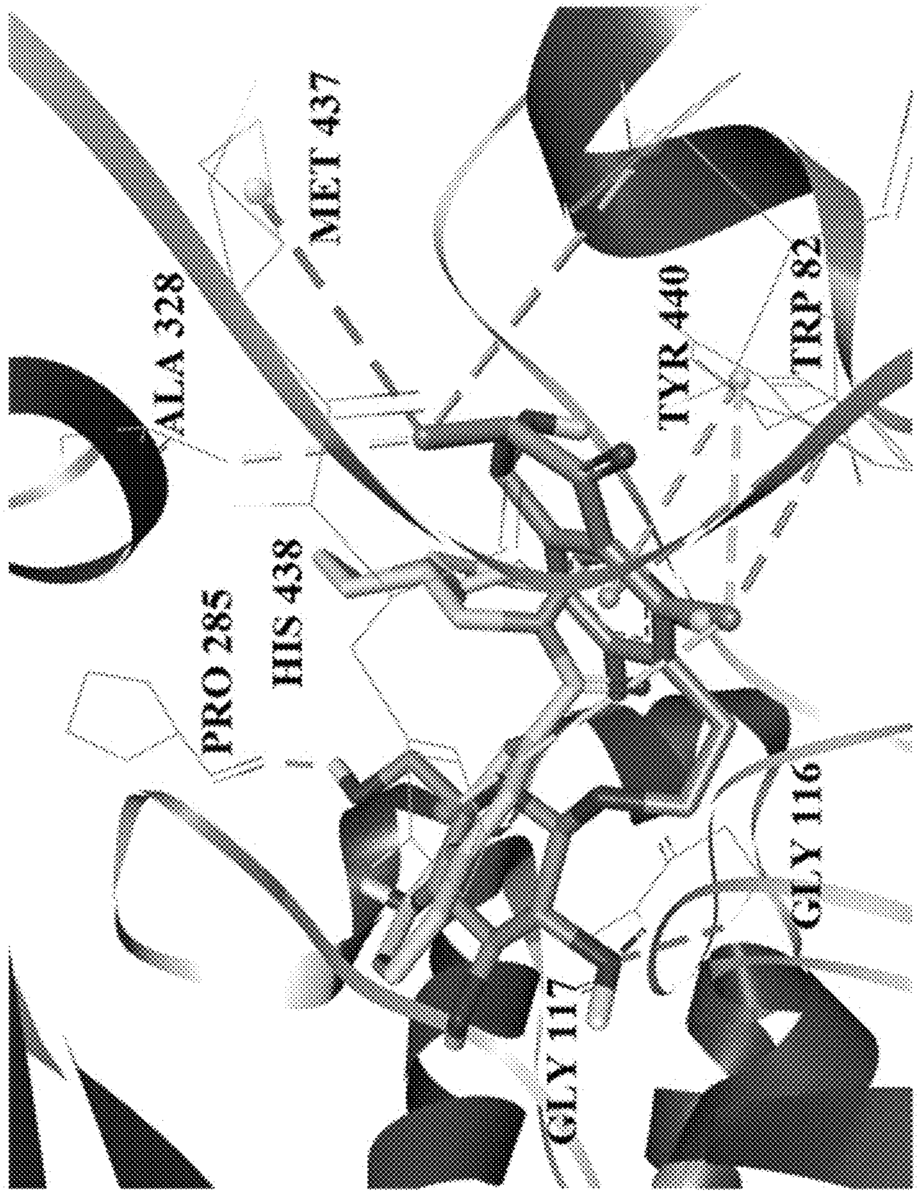
FIG. 15 illustrates the interaction of (2R, 3R)-pteroside C (Compound 16) with human BACE1 in a 3D image (15*a*) and a plane image (15*b*), wherein the green color accounts for a hydrogen bond, the pink for hydrophobic interaction, and the purple color for a n-sigma bond.
Figure 15B:
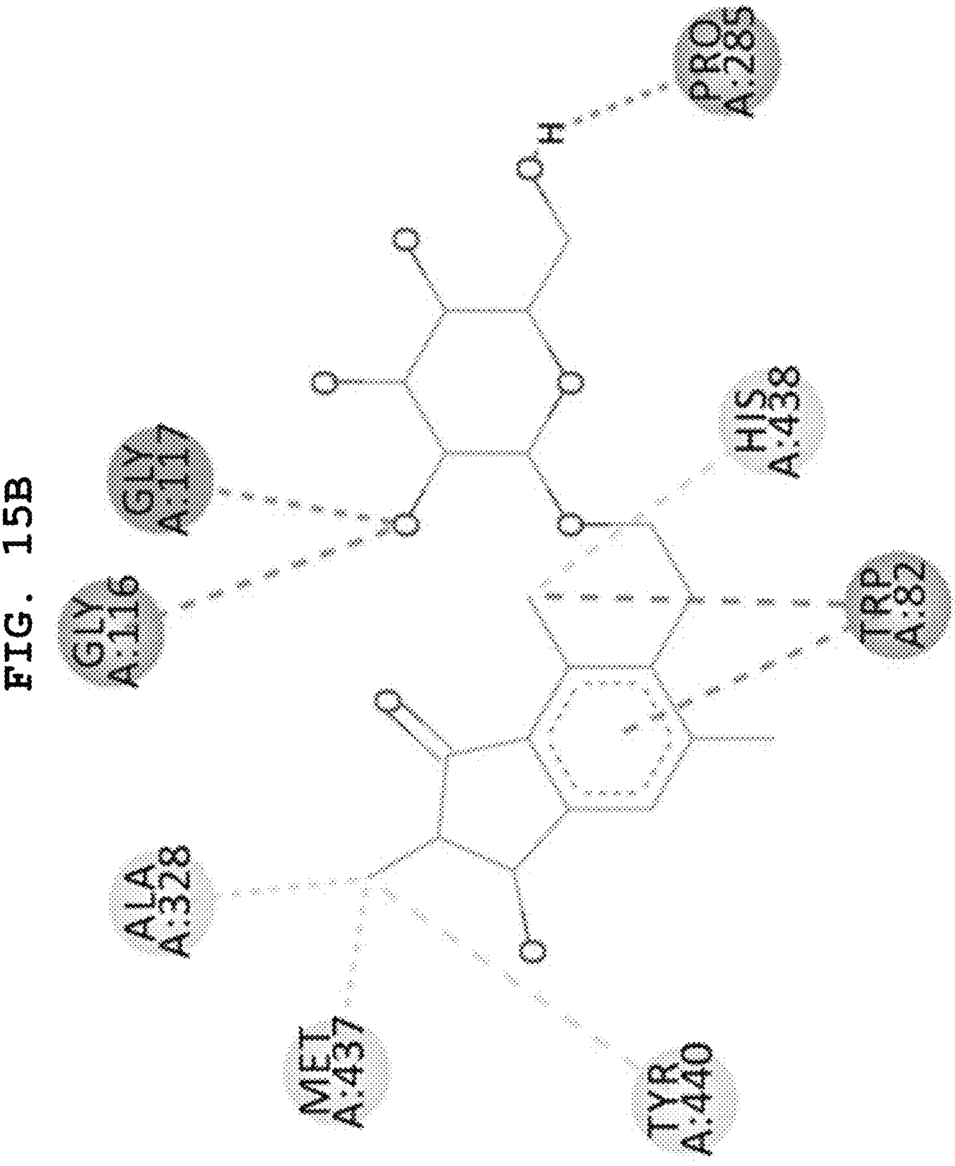

FIGS. 13 to 15 are images showing the binding of (2R, 3R)-pteroside C to BACE1, AChE, and BChE, respectively.

Consequently, pterosin and derivatives thereof have promising inhibitory potentials against BACE1, AChE, and BChE, as proven by the in vitro enzyme assay and the molecular docking simulation. Taken together, the data obtained above suggest that the compounds of the present disclosure can be used in therapeutic or preventive agents for dementia thanks to the inhibitory activity thereof against BACE1 and AChE.

INDUSTRIAL APPLICABILITY

As described hitherto, the method of the present disclosure can be advantageously used for using the pterosin compounds extracted from bracken ferns or derivatives thereof to provide a therapeutic agent for preventing or treating degenerative brain disease or a food composition for alleviating degenerative brain disease or enhancing a cognitive function.

The invention claimed is:

1. A method for treating or alleviating Alzheimer's disease in a human, the method consisting essentially of administering to the human in need thereof a therapeutically effective amount of a purified composition from a bracken fern consisting of a compound defined by Chemical Formula 1 or a salt thereof as an effective ingredient:

[Chemical Formula]

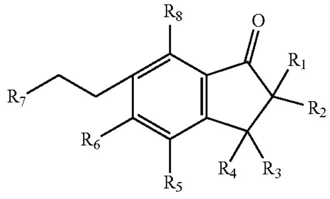

wherein, $R_1$, $R_2$, $R_3$, $R_4$, $R_5$, $R_6$, and $R_8$ are each independently H, OH, an alkyl or alcohol of 1 to 4 carbon atoms, or alkyl-O-glucose; and $R_7$ is one selected from the group consisting of halogen, H, OH, O-alkyl, O-alkenyl, O-alkynyl, O-alcohol, O-carboxyl, O-ether, O-sulfonic acid (—$SO_3H$), O-cycloalkyl, O-heterocycloalkyl, glucose, and O-glucose, wherein the compound is selected from the group consisting of (2R)-Pterosin B, (2R,3R)-Pterosin C, (2S,3R)-Pterosin C, (2R)-Pteroside B, (2S,3R)-Pteroside C, (2R,3R)-Pteroside C, (3R)-Pterosin D and (3S)-Pteroside D.

* * * * *